【12】 United States Patent
Huang et al.

(10) Patent No.: US 11,980,594 B2
(45) Date of Patent: May 14, 2024

(54) COMPOSITION AND METHOD FOR TREATING A DRUG-RESISTANT CANCER

(71) Applicant: NOVELWISE PHARMACEUTICAL CORPORATION, Taipei (TW)

(72) Inventors: Chung-Yang Huang, Taipei (TW); Chia-Chung Hou, Taipei (TW)

(73) Assignee: NOVELWISE PHARMACEUTICAL CORPORATION, Taipei (TW)

( * ) Notice: Subject to any disclaimer, the term of this patent is extended or adjusted under 35 U.S.C. 154(b) by 0 days.

(21) Appl. No.: 17/828,983

(22) Filed: May 31, 2022

(65) Prior Publication Data
US 2023/0038230 A1 Feb. 9, 2023

Related U.S. Application Data

(60) Provisional application No. 63/194,585, filed on May 28, 2021.

(51) Int. Cl.
*A61K 31/085* (2006.01)
*A61K 31/495* (2006.01)
*A61P 35/00* (2006.01)

(52) U.S. Cl.
CPC .......... *A61K 31/085* (2013.01); *A61K 31/495* (2013.01); *A61P 35/00* (2018.01)

(58) Field of Classification Search
CPC .................................................. A61K 31/085
See application file for complete search history.

(56) References Cited

PUBLICATIONS

Vippagunta et al. (2001).*
Wolff et al (1976).*
Banker et al (1978).*
Santos-Barriopedro et al., "HDAC8 affects MGMT levels in glioblastoma cell lines via interaction with the proteasome receptor ADRM1", Genes & Cancer, vol. 10, Nos. 5-6, 2019, pp. 119-133.
Yang et al. "NBM-T-L-BMX-OS01, Semisynthesized from Osthole, Is a Novel Inhibitor of Histone Deacetylase and Enhances Learning and Memory in Rats", Evidence-Based Complementary and Alternative Medicine, vol. 2013, Article ID 514908, 2013, pp. 1-18.

* cited by examiner

*Primary Examiner* — Paul V Ward
(74) *Attorney, Agent, or Firm* — Birch, Stewart, Kolasch & Birch, LLP

(57) ABSTRACT

The present invention provides a combination and method for treating a Temozolomide (TMZ)-resistant cancer patient, which comprises a combination of TMZ and an isoform-selective HDAC8 inhibitor, such as BMX at an effective relative ratio to overcome TMZ resistance by enhancing TMZ-mediated cytotoxic effect by downregulating the β-catenin/c-Myc/SOX2 signaling pathway and upregulating WT-p53 mediated MGMT inhibition.

19 Claims, 22 Drawing Sheets
(6 of 22 Drawing Sheet(s) Filed in Color)
Specification includes a Sequence Listing.

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(20)

<400> SEQUENCE: 1
```

```
gcgtgatttc cagcacataa                                            20

<210> SEQ ID NO 2
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(20)

<400> SEQUENCE: 2
atacttgacc ggggtcatcc                                            20

<210> SEQ ID NO 3
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(21)

<400> SEQUENCE: 3
tcaagtgcag tgcaacaact c                                          21

<210> SEQ ID NO 4
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(22)

<400> SEQUENCE: 4
agaggacagg gtggagtaat ca                                         22
```

COMPOSITION AND METHOD FOR TREATING A DRUG-RESISTANT CANCER

CROSS REFERENCE

This non-provisional application claims the priority under 35 U.S.C. § 119(a) on U.S. Patent Provisional Application No. 63/194,585 filed on May 28, 2021, the entire contents of which are hereby incorporated by reference.

REFERENCE TO AN ELECTRONIC SEQUENCE LISTING

The contents of the electronic sequence listing (NW0012US_ST25.txt; Size: 1,222 bytes; and Date of Creation: Sep. 9, 2022) is herein incorporated by reference in its entirety.

FIELD OF THE INVENTION

The present invention pertains to a new composition and method for treating a drug-resistant cancer, particularly a TMZ-resistant cancer.

BACKGROUND OF THE INVENTION

Glioblastoma multiforme (GBM) is one of the most malignant tumors, and it has an aggressive pattern and a high recurrence rate; it is a World Health Organization grade IV astrocytoma [1]. Despite multimodalities treatment with surgery and concomitant radiation and chemotherapy, patients with GBM still have a poor prognosis, with a mean survival of less than 15 months, which indicates therapeutic resistance [2-4].

Colon cancer or colorectal cancer (CRC) is one of the most prevalent kinds of malignancy tumors and the third leading cause of cancer mortality globally. Although colon cancer or CRC standard treatment was already well studied and established, it still remains high mortality and clinical challenge issues. The disease is less symptomatic since patients are frequently diagnosed with advanced cancer at an initial evaluation, and the consequent five-year survival rate is around 10% [5-6]. The standard treatments of CRC are surgery, radiation and/or chemotherapy, in which Oxaliplatin (Oxp) and its prodrug capecitabine are widely used in clinical practice [7-8]. Unfortunately, the recurrence under this kind of DNA crosslink agent treatment is still common within the first few years even after completing the whole cycle [9].

Temozolomide (TMZ) is an imidazotetrazine lipophilic prodrug of the alkylating agent dacarbazine with good penetration of the blood-brain barrier. TMZ is though spontaneous nonenzymatic conversion at physiologic pH to the reactive compound 5-(3-methyltriazen-1-yl)-imidazole-4-carboxamide (MTIC)[10]. The cytotoxicity of MTIC is thought to be primarily due to alkylation (methylation) of DNA, which occurs mainly at the O6 and N7 positions of guanine. TMZ has been widely used as the standard chemotherapy for newly-diagnosed glioblastoma multiforme (GBM) since its initial FDA approval in 2005. Besides GBM, TMZ has been proven to have equal efficacy to dacarbazine. Therefore, it is also used "off-label" in patients with malignant melanoma after standard treatment. In addition, many clinical studies are ongoing to demonstrate the effectiveness of TMZ in other indications, such as brain metastases, lymphomas, neuroendocrine tumors, pituitary tumors, Ewing's sarcoma, primitive neuroectodermal tumors, refractory leukemia, lung cancer, and other tumors [11]. TMZ is a well-tolerated treatment for elderly, pediatric, or palliative patients in clinical, which can be used as a single agent or as an adjuvant (radiotherapy or chemotherapy) first-line or x-line treatment. However, the drug resistance of TMZ-treated patients will happen due to the over-expression of O6-methylguanine methyltransferase (MGMT). Therefore, it is a clinically meaningful and substantial obstacle that must be overcome to treat GBM successfully.

However, less than 50% of patients respond to TMZ due to the overexpression of O6-methylguanine methyltransferase (MGMT), which reverses the methylation of the O6 position of guanine, thereby repairing DNA in GBM cells and resisting the chemotherapeutic effect [12-14]. Comparing the MGMT protein level between newly diagnostic and recurrent CRC patients who had received TMZ treatment supported MGMT reduction may promote efficacy of TMZ treatment[15-17]. In addition to promoter methylation, MGMT is regulated by various transcription factors, such as p53, Sp1, NF-κB, CEBP, and AP-18. Among these, p53 downregulates MGMT transcription by directly interacting with the MGMT promoter [18,19]. Thus, in addition to MGMT promoter methylation, p53 could regulate MGMT expression and cause TMZ resistance. Therefore, additional mechanisms regulating MGMT must be identified to overcome TMZ resistance.

Accordingly, it is desirable to develop a new and better therapy or treatment for a drug-resistant cancer, particularly TMB-resistant GBM or CRC.

SUMMARY OF THE INVENTION

Accordingly, the present invention provides a new method for treatment of a drug-resistant cancer, such as TMZ-resistant GBM or CRC.

It is unexpectedly found in the present invention that a compound X, such as BMX, can enhance the TMZ-mediated cytotoxic effect on GBM-R cell lines and CRC cell lines HT29, HCT116 and RKO. Accordingly, the present invention provides a new method for treatment of a drug-resistant cancer in a patient, particularly TMZ-resistant GBM or CRC, comprising administering said patient a combination of BMX and TMZ.

In the invention, BMX (NBM-T-L-BMX-OS01) which is a histone deacetylase 8 inhibitor (HDAC8i), shows significantly anti-cell proliferation effects in colorectal cancer cell, human umbilical endothelial cells, lung cancer cells and glioblastoma cell, and it also presents tumor suppression ability in animal xenograph model [20, 21]. However, it is unexpectedly found in the present invention that BMX could overcome drug-resistance in cancer cells. In one example of the invention BMX could overcome GBM-R cells by enhancing the TMZ-mediated cytotoxic effect by downregulating the β-catenin/c-Myc/SOX2 signaling pathway and upregulating p53-mediated MGMT inhibition. It was confirmed that high HDAC8 expression in human GBM tissues and GBM-R cell lines correlated with MGMT levels, and the combination of BMX and TMZ induced WT(Wild Type)-p53 mediated apoptosis through WT-p53 mediated MGMT inhibition in GBM-R cell lines. Moreover, the combination of BMX and TMZ suppressed cell proliferation and GSC phenotype activity via the β-catenin/c-Myc/cyclin D1/SOX2 signaling pathway in GBM-R cell lines.

In one example of the invention, it was evidenced that a combination of BMX and TMZ triggered on cell cycle arrest, senescence, autophagy and apoptosis in CRC cells via upregulating p53/p21/Puma/Bax is compromised by the crosstalk of the downregulating Wnt/β-catenin/cyclin D1/c-Myc/p62 pathways. Accordingly, BMX could be a promising strategy for the precision personal treatment of TMZ-resistant GBM patients or CRC patients with WT-p53.

Accordingly, in one aspect, the present invention provides a combination for treating a TMZ-resistant cancer, which comprises TMZ and a compound A having the structure of Formula A, or a pharmaceutically acceptable salt, stereoisomer, enantiomer, prodrug or solvate thereof:

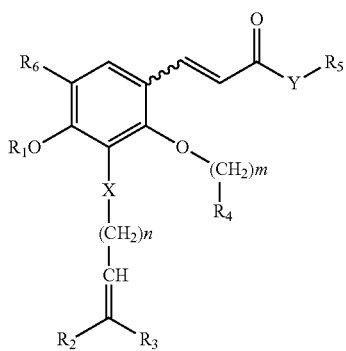

Formula A wherein $R^1$ is hydrogen, alkyl, alkenyl, $C_5$-$C_6$ cycloalkyl, 5-membered or 6-membered unsaturated carbocycle or 5-membered or 6-membered heterocycle, or $(CH_2)mR^4$;

X is C, —O—, —N— or —S—;

Y is —O—, —NH or —O—$C_1$-$C_4$ alkyl;

n is an integer of 0 to 10;

m is an integer of 0 to 5;

$R^2$ and $R^3$ is independently $C_1$-$C_6$ alkyl;

$R^4$ is $C_5$-$C_6$ cycloalkyl or 5-membered or 6-membered unsaturated carbocycle or heterocycle which may be substituted with halogen, —$CF_3$, —$OR^7$ or —$NR^7R^8$, wherein $R^7$ and $R^8$ are independently hydrogen or $C_1$-$C_6$ alkyl;

$R^5$ is OH, $NH_2$ or $C_5$-$C_6$ cycloalkyl, 5-membered or 6-membered unsaturated carbocycle or heterocycle wherein the cycloalkyl, carbocycle and heterocycle may be optionally substituted with halogen, $NH_2$, $NO_2$, $C_1$-$C_6$ alkoxy, $C_{1-6}$ alkylthio, $OR^{7''}$, $NR^7R^8$ or $CF_3$; and $R^6$ is H, $C_1$-$C_{10}$ alkyl which may be substituted by hydroxy or $C_2$-$C_{10}$ alkenyl, or together with $R_1$ being —$C_2H_2$—; and wherein TMZ and the compound A are combined at a relative ratio to effectively overcome TMZ resistance.

In one embodiment of the invention, the compound A is a compound BMX having the structure of

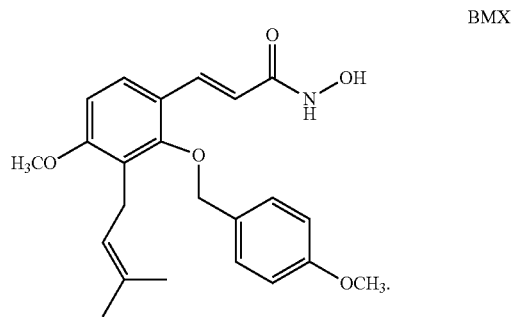 [SMILES: COc1ccc(COc2c(/C=C/C(=O)NO)ccc(OC)c2CC=C(C)C)cc1]

BMX

According to the present invention, the TMZ resistance is overcome by enhancement of TMZ-mediated cytotoxic effect by downregulating the β-catenin/c-Myc/SOX2 signaling pathway and upregulating WT-p53 mediated MGMT inhibition.

In the invention, TMZ and the compound A, e.g., BMX, are separately or sequentially administrated.

In one example of the invention, the cancer is glioblastoma multiforme (GBM) or colorectal cancer (CRC).

In another aspect, the present invention provides a method for treating a TMZ-resistant cancer in a patient, which administering the patient a therapeutically effective amount of the combination according to the invention.

In one example of the invention, the cancer is GBM or CRC.

In a further aspect, the present invention provides a method for treating precision personal treatment for a drug-resistant cancer in a patient, comprising determining the expression of WT-p53 in the patient, and administering the patient a therapeutically effective amount of BMX or its combination with said drug if the expression of WT-p53 is present in the patient.

In one embodiment of the invention, the drug is TMZ.

In one particular embodiment of the invention, the drug-resistant cancer is TMZ-resistant cancer, particularly GMB or CRC.

In the invention, it is confirmed that BMX is effective in enhancing inhibition of WT-p53 cancer cells.

In a further aspect, the present invention provides a use of the combination of BMX and TMZ for manufacturing a medicament or a kit for treating a TMZ-resistant cancer.

The present invention will be further described by way of the following examples. However, it should be understood that the following examples are solely intended for the purpose of illustration and should not be construed as limiting the present invention in practice.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred.

In the drawings:

Figure 1:
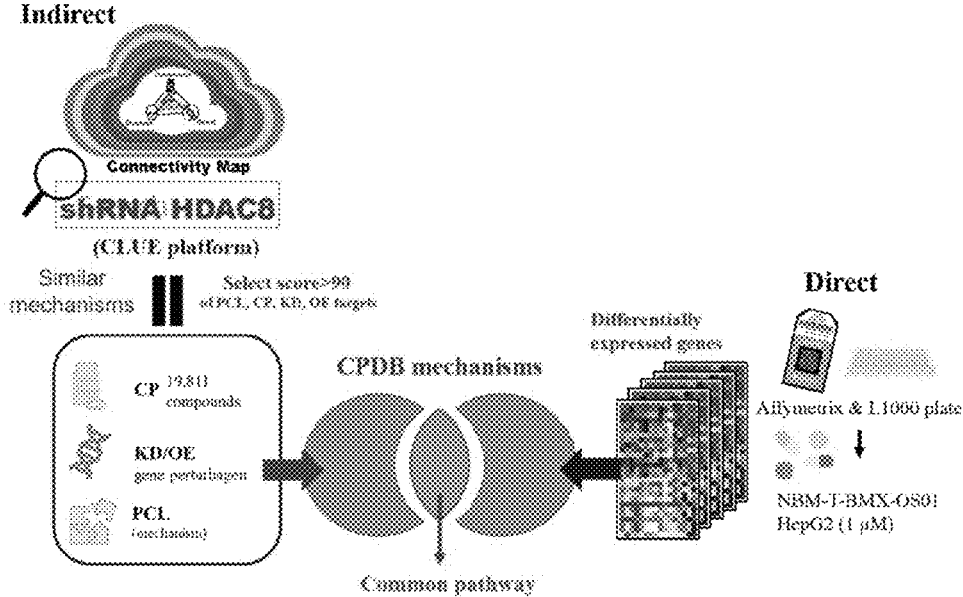
Figure 1:
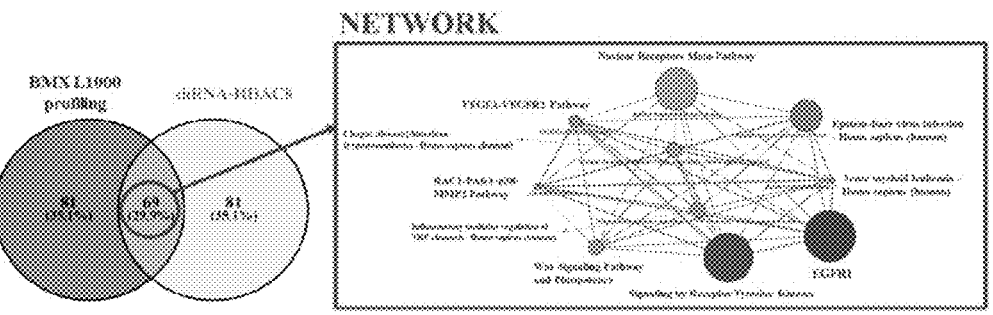
Figure 1:
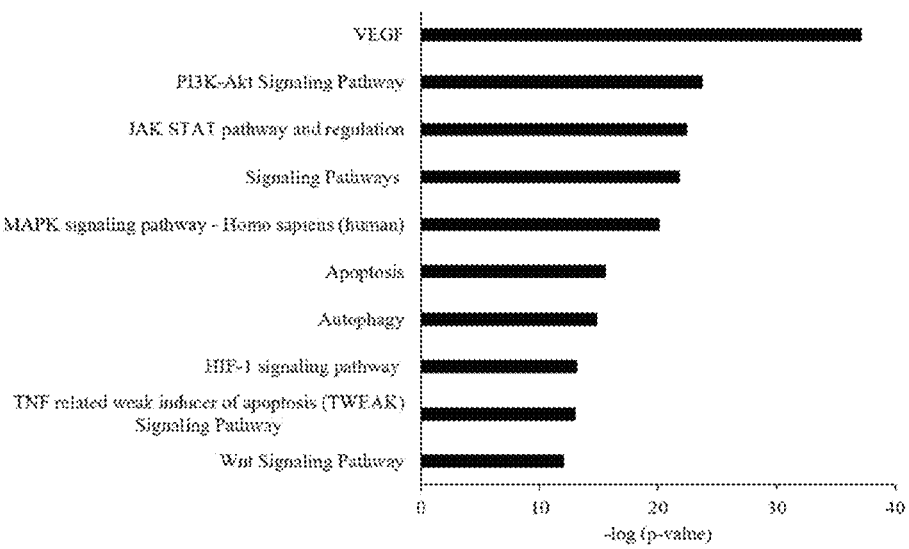

FIG. 1 provides the pathway analysis for genes potentially associated with HDAC8 by bioinformatics tools; wherein shRNA HDAC8 was entered into the CLUE database, and CP and PCL with a score of >90 were selected (A). The target genes were entered into the CPDB pathway analysis database (B) for further experiments. (C) Top 10 pathways for selecting CP and PCL (score>90) for shRNA HDAC8. 10 pathways as below: VEGF; PI3K-Akt Signaling Pathway; JAK STAT pathway and regulation; Signaling Pathway; MAPK signaling pathway—*Homo sapiens* (human); Apoptosis; Autophagy; HIF-1 signaling pathway; TNF related weak inducer of apoptosis (TWEAK) Signaling Pathway; Wnt Signaling Pathway. VEGF; PI3K-Akt Signaling Pathway; JAK STAT pathway and regulation; Signaling Pathway; MAPK signaling pathway—*Homo sapiens* (human); Apoptosis; Autophagy; HIF-1 signaling pathway; TNF related weak inducer of apoptosis (TWEAK) Signaling Pathway; Wnt Signaling Pathway.

Figure 2:
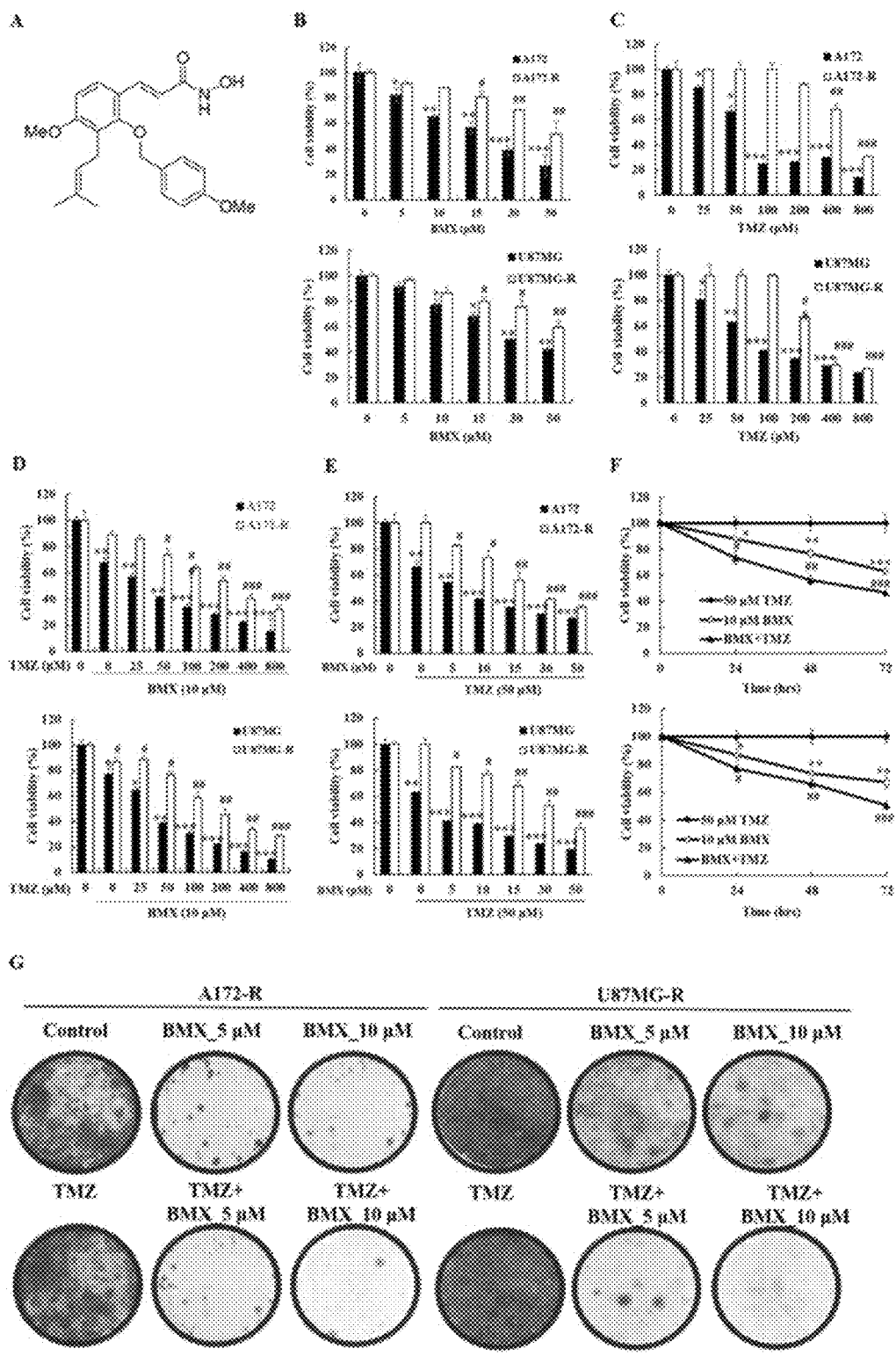

FIG. 2 shows that BMX inhibited the growth and proliferation of GBM cells (U87MG and A172) and the BMX and TMZ combination inhibits the growth and proliferation in GBM-R cells (U87MG-R and A172-R). (A) Chemical structure of BMX. (B) Cell viability of GBM and GBM-R cell lines after treatment with 0.5, 10, 15, 30, or 50 µM BMX. (C) Cell viability of GBM and GBM-R cell lines after treatment with 0.25, 50, 100, 200, 400, or 800 µM TMZ. (D) GBM and GBM-R cell viability after treatment with 10 µM BMX with or without TMZ at various concentrations (0.25, 50, 100, 200, 400, or 800 µM) for 24 hrs. (E) GBM and GBM-R cell viability after treatment with 50 µM TMZ with or without BMX at various concentrations (0.5, 10, 15, 30, or 50 µM) for 24 hrs. (F) GBM-R cell viability after treatment with 50 µM TMZ with or without 10 µM BMX for 24, 48, and 72 hrs. (G) Colony formation assay of GBM and GBM-R cell lines with BMX (0, 5, or 10 µM) with or without TMZ (50 µM) for 14 days. Data are represented as means±SEM from three experiments. *$p<0.05$ vs. control (A172 and U87MG); #$p<0.05$ vs. (A172-R and U87MG-R).

Figure 3:
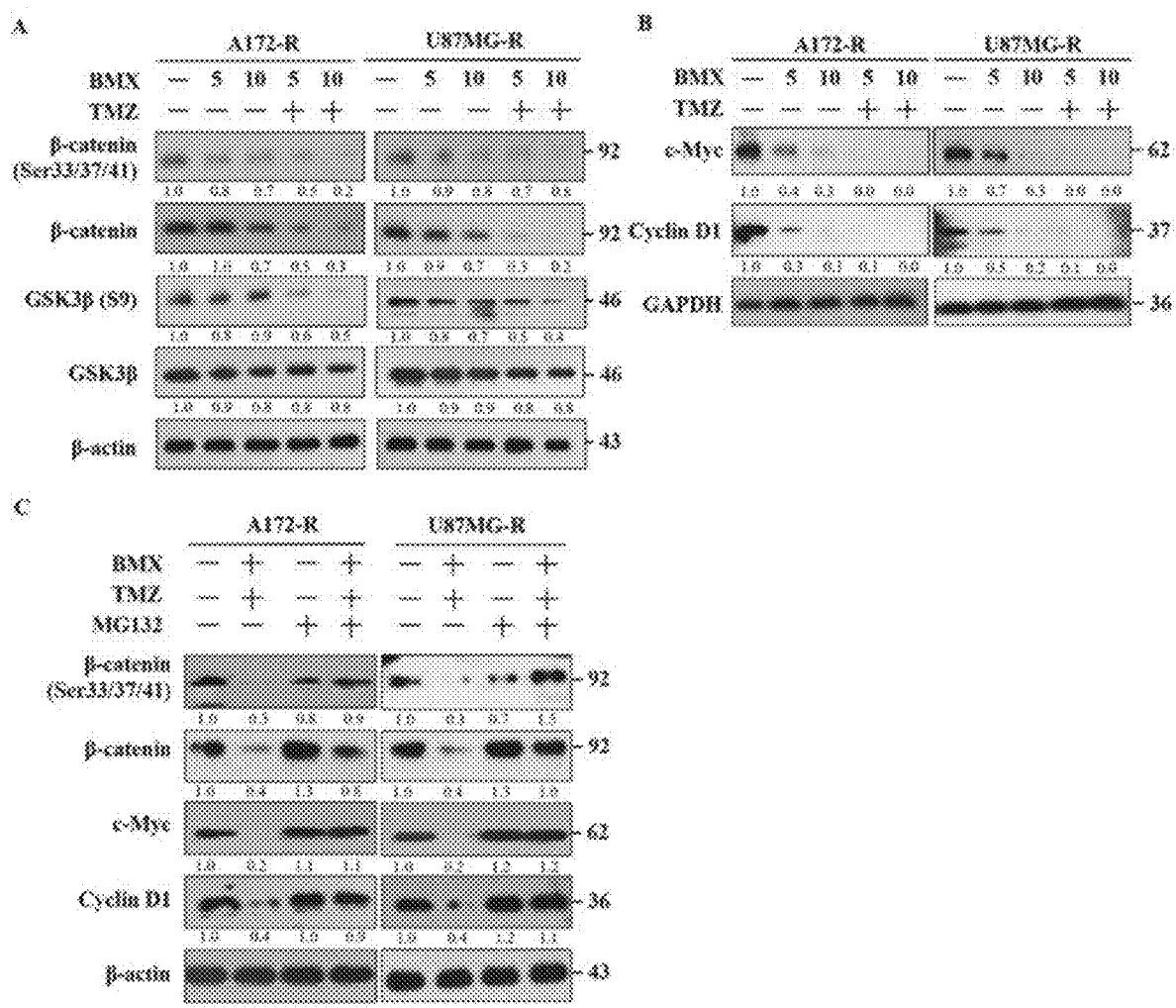

FIG. 3 shows that BMX enhanced the TMZ-mediated cytotoxic effect by targeting the Wnt/β-catenin/GSK3β pathway to suppress cell proliferation in GBM-R cells. (A) GSK-3β and β-catenin activation status of GBM-R cells after treatment with 5 or 10 µM BMX with or without 50 µM TMZ for 48 hrs. (B) c-Myc and cyclin D1 protein levels of GBM-R cells after treatment with 5 or 10 µM BMX with or without 50 µM TMZ for 48 hrs. (C) β-catenin (Ser33/37/41) phosphorylation status and changes in c-Myc and cyclin D1 protein expression in GBM-R cells after treatment with 10 µM BMX and 50 µm TMZ with or without 10 µM MG132.

FIGS. 4A-4E show that BMX and TMZ combination enhanced the TMZ-mediated cytotoxic effect by promoting TMZ-mediated apoptosis in GBM-R cells. (A) Cell cycle distribution of GBM (U87MG and A172) and GBM-R (U87MG-R and A172-R) cells treated with BMX for 48 hrs with or without a TMZ. (B) Percentages of cells in G0/G1, S and G2/M phases are presented in the histograms. (C) Bar graph of the percentage of sub-G1. (D) Annexin V/PI apoptosis assay of GBM (U87MG and A172) and GBM-R (U87MG-R and A172-R) cells treated with BMX for 48 hrs with or without TMZ. (E) Histograms illustrating the percentages of apoptotic cells.

Figure 5:
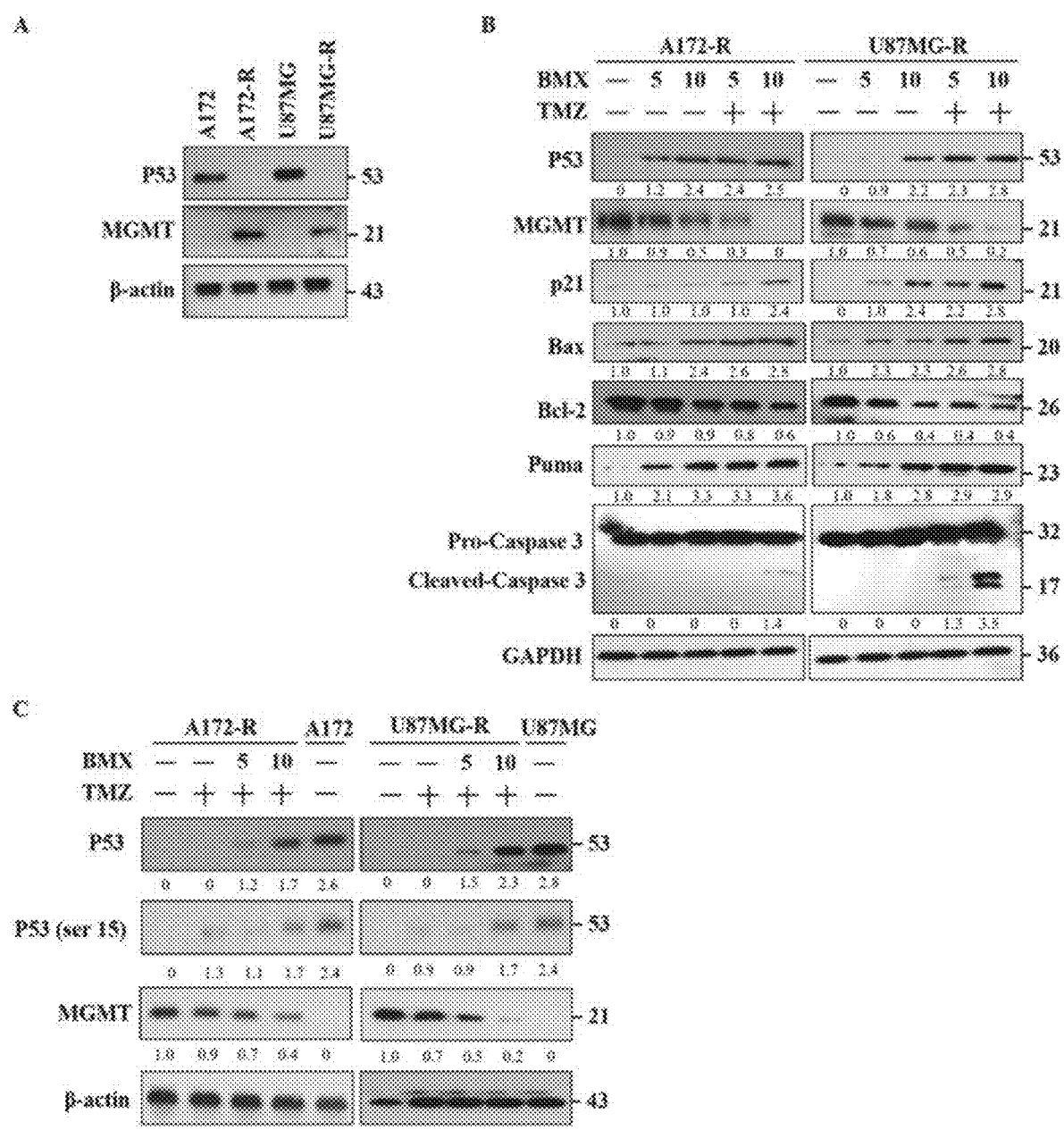

FIG. 5 shows that the combination of BMX and TMZ enhanced the TMZ-mediated cytotoxic effect by WT-p53 mediated MGMT inhibition in GBM-R cells. (A) The expression pattern of WT-p53 and MGMT on the GBM (U87MG and A172) and GBM-R (U87MG-R and A172-R) cell lines. (B) Protein alterations of WT-p53, MGMT, P21, Bax, Bcl-2, Puma, and cleaved caspase-3 after treatment with 5 or 10 µM BMX with or without 50 µM TMZ for 48 hrs on U87MG-R and A172-R cells. (C) Treatment of GBM (U87MG and A172) and GBM-R (U87MG-R and A172-R) cells with 5 or 10 µM BMX with or without 50 µM TMZ for 48 hrs reduced MGMT levels and increased WT-p53 and Phospho-WT-p53 levels (ser 15). β-actin was used as an internal control.

Figure 6:
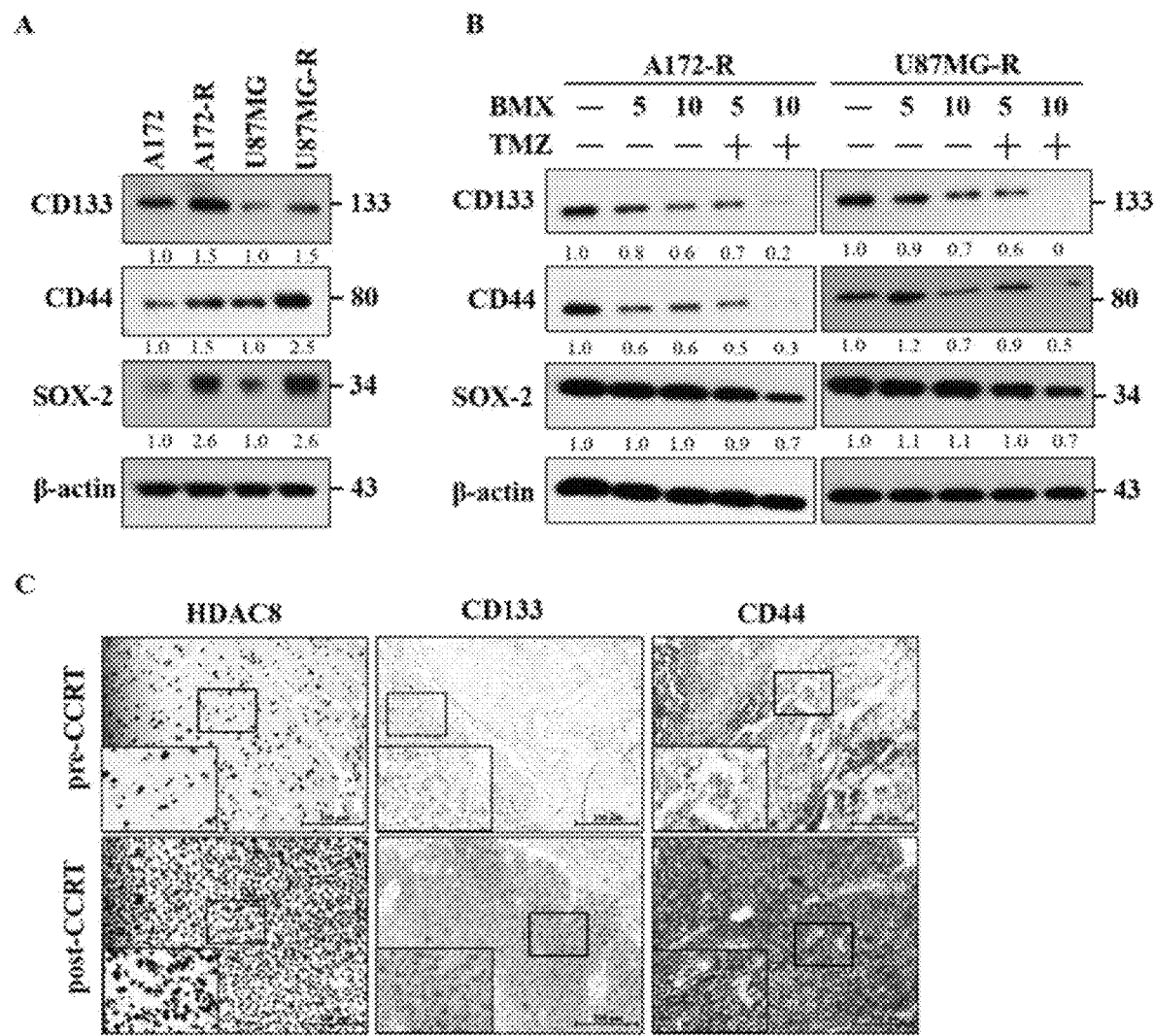

FIG. 6 shows that the combination of BMX and TMZ reduced GSC formation in GBM-R cells. (A) Status of CSC-related genes (CD133, CD44, and SOX2) expression between parental and resistant daughter cell lines. (B) Changes in CD133, CD44, and SOX2 protein levels after receiving 5 and 10 µM BMX with or without 50 µM TMZ for 48 hrs on U87MG-R and A172-R cells. (C) Immunohistochemical staining for HDAC8 and CSC-related genes (CD133 and CD44) in human primary GBM (the same patient before concomitant radiation and chemotherapy) and recurrent GBM tumor tissues (after concomitant radiation and chemotherapy) obtained through surgical biopsies.

Figure 7:
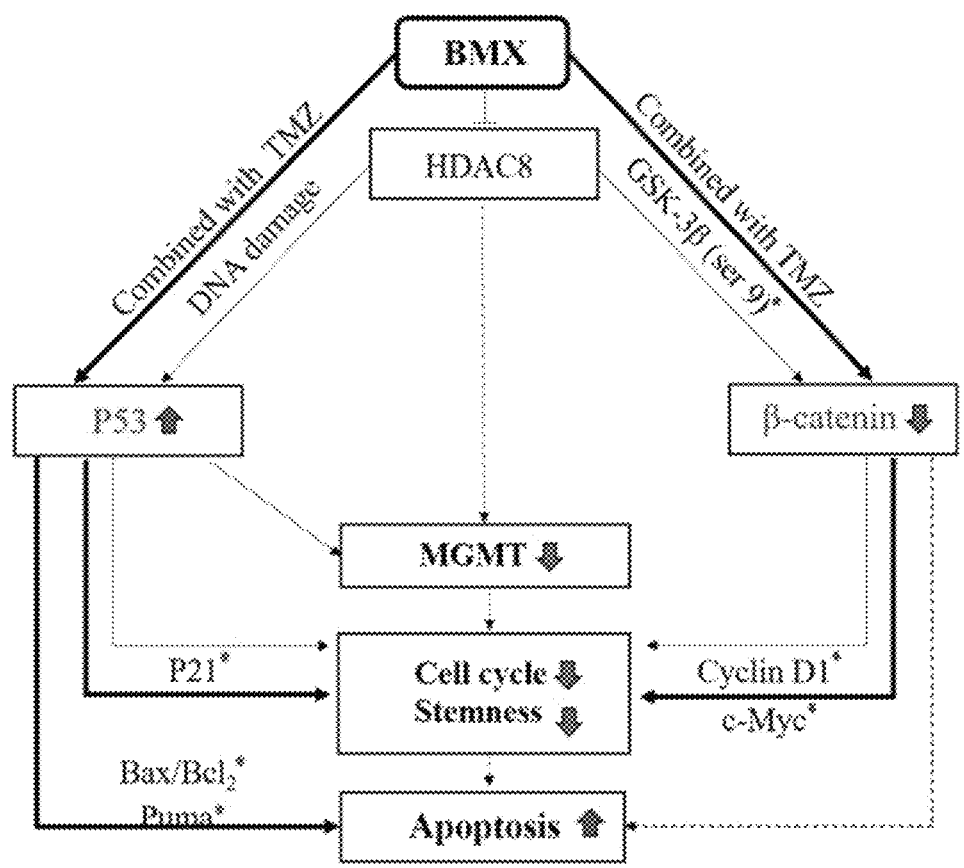

FIG. 7 provides a working model of the mechanism of combination of BMX with TMZ to overcome TMZ resistance in GBM-R cells.

Figure 8:
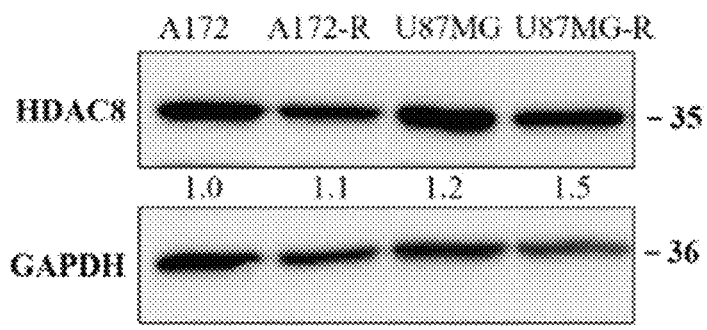
Figure 8:
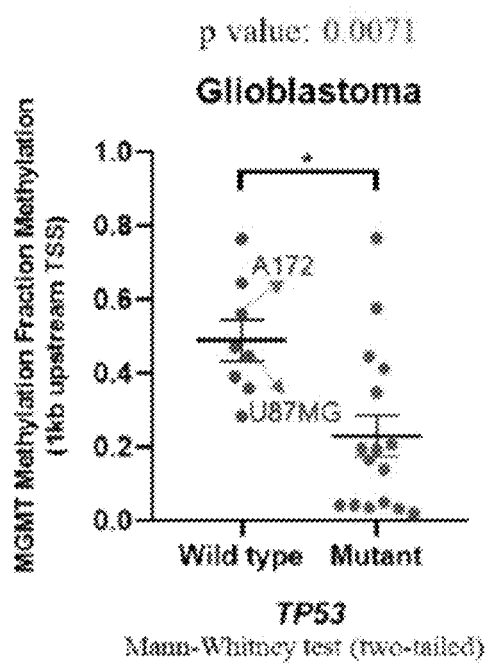

FIG. 8 shows the gentic features of GBM cell lines. (A) The expression of HDAC8 from Abcam company in GBM cells by western blot. (B) Scatter plot for p53 WT and mutant cells.

Figure 9:
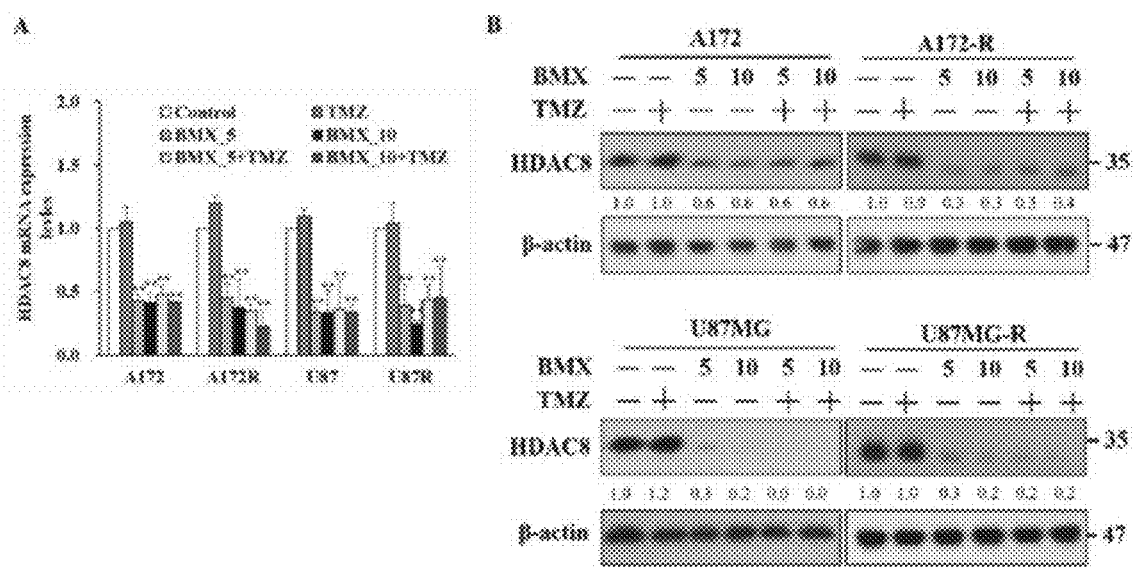

FIG. 9 shows that BMX was a potent semi synthesized HDAC8 inhibitor. (B) The examination of MGMT methylation pairs GBM through big data analysis. The wide-type and mutant are labeled with blue and red, respectively (one-sided t test,*: $p<0.05$). (A) HDAC8 expression levels stimulated with different doses of BMX (0-10 µM) in the presence or absence of TMZ (50 µM) were determined using qRT-PCR assays. (B) HDAC8 expression levels stimulated with BMX (0-10 µM) with or without TMZ (50 µM) were determined using Western blotting.

FIGS. 10A-10D show that BMX and BMX with TMZ inhibited the growth and proliferation of U87MG, U87MG-R, A172 and A172-R. (A) Cell viability of GBM and GBM-R cell lines after treating with indicated concentrations of BMX (0.5, 10, 15, 30 or 50 µM) for 24, 48 and 72 hrs. (B) Cell viability of GBM and GBM-R cell lines after treating with the indicated concentrations of TMZ (0.25, 50, 100, 200, 400 or 800 µM) 24, 48 and 72 hrs. (C) Cell viability of GBM and GBM-R cells lines after treating with 10 µM BMX with or without TMZ at different concentrations (0.25, 50, 100, 200, 400 or 800 µM for 24, 48 and 72 hrs. (D) Cell viability of GBM and GBM-R cells lines after treating with 50 µM TMZ with or without BMX at different concentrations (0.5, 10, 15, 30 or 50 µM) for 24, 48 and 72 hrs. (E) Cell viability of GBM-R cells lines after treating with 50 µM TMZ with or without 10 µM BMX for 24, 48 and 72 hrs.

Figure 11:
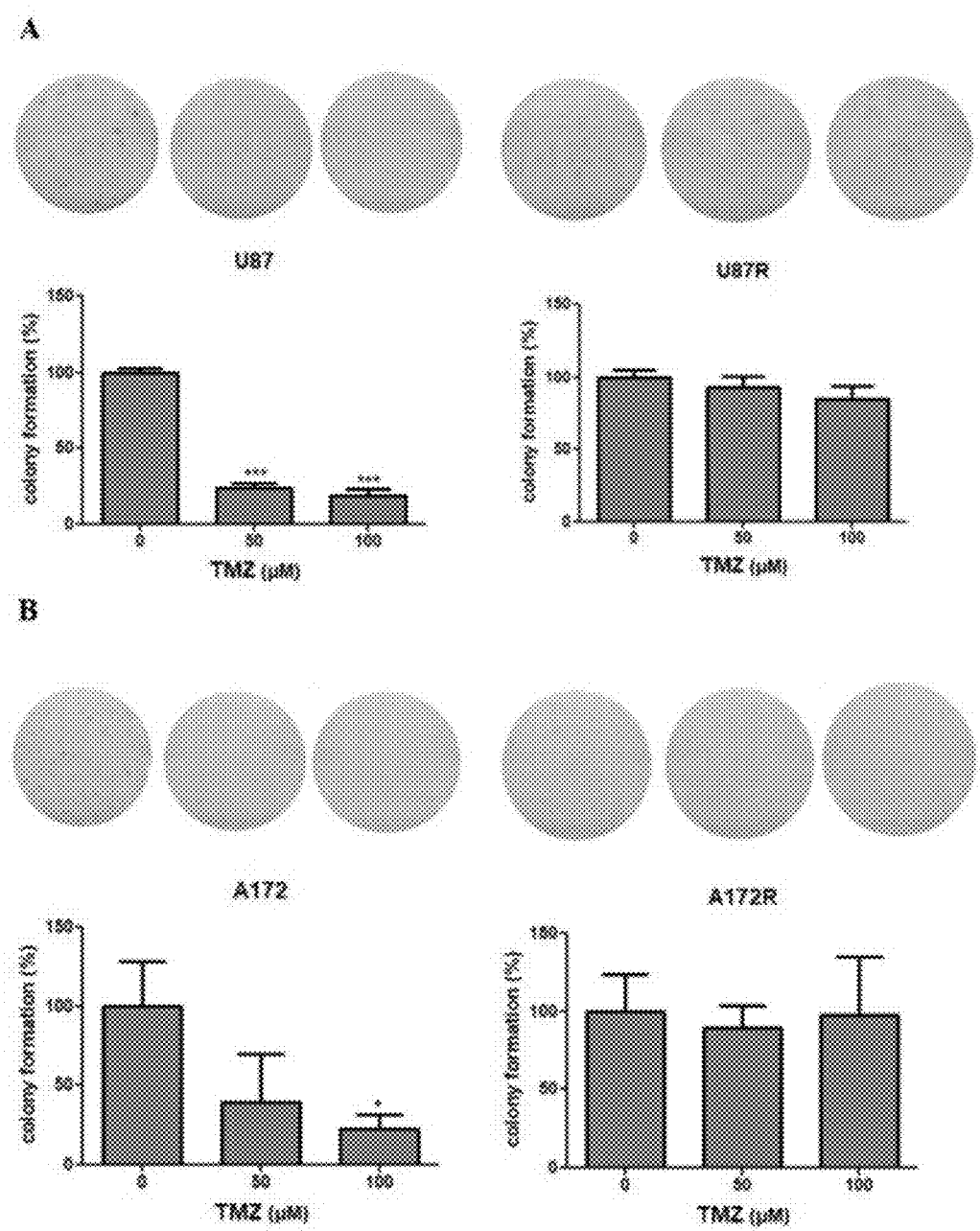

FIG. 11 shows that in vitro cytotoxicity of BMX in GBM cells. (A) U87 and U87R cells and (B) A172 and A172R cells were treated with TMZ (50 and 100 µM). This inhibitory effect of TMZ on GBM cells was determined using a clonogenic assay. *$p<0.05$; $p<0.01$; *$p<0.001$.

Figure 12:

FIG. 12 shows the drug and gene information in Glioblastoma, including the HDAC8 expression levels of two parent GBM cell lines (A172 and U87MG), which are wild-type p53 (WT-p53), and two TMZ-resistant GBM cell lines.

Figure 13:
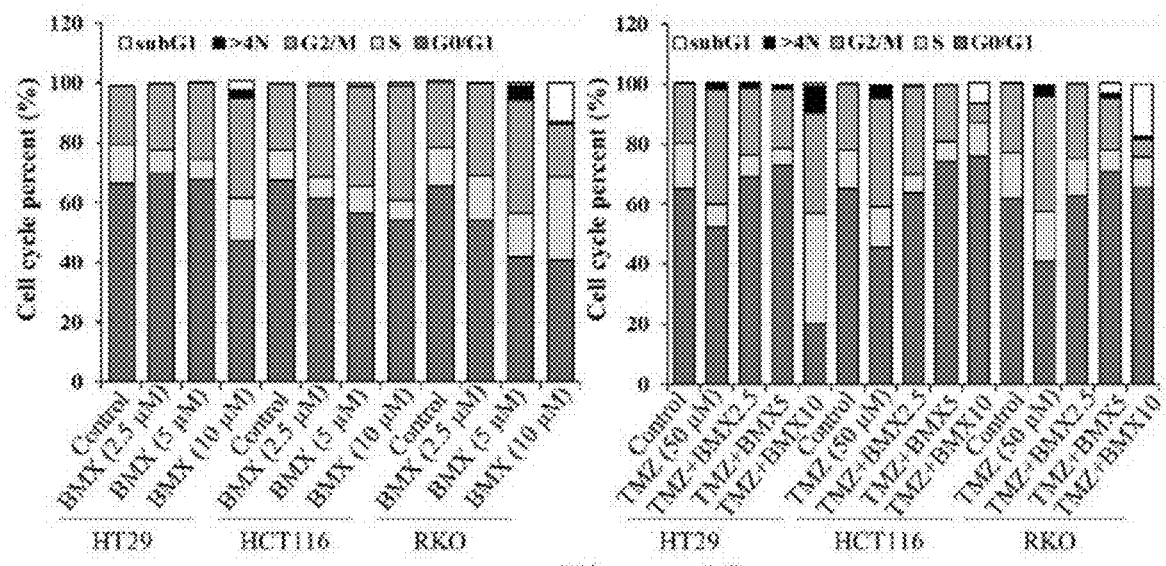

FIG. 13 shows the results of cell cycle analysis after 48 hrs treatment with different concentrations of BMX or BMX combined with TMZ in HT29, HCT116 and RKO cells and the proportion of cells in each cell cycle phase.

Figure 14:
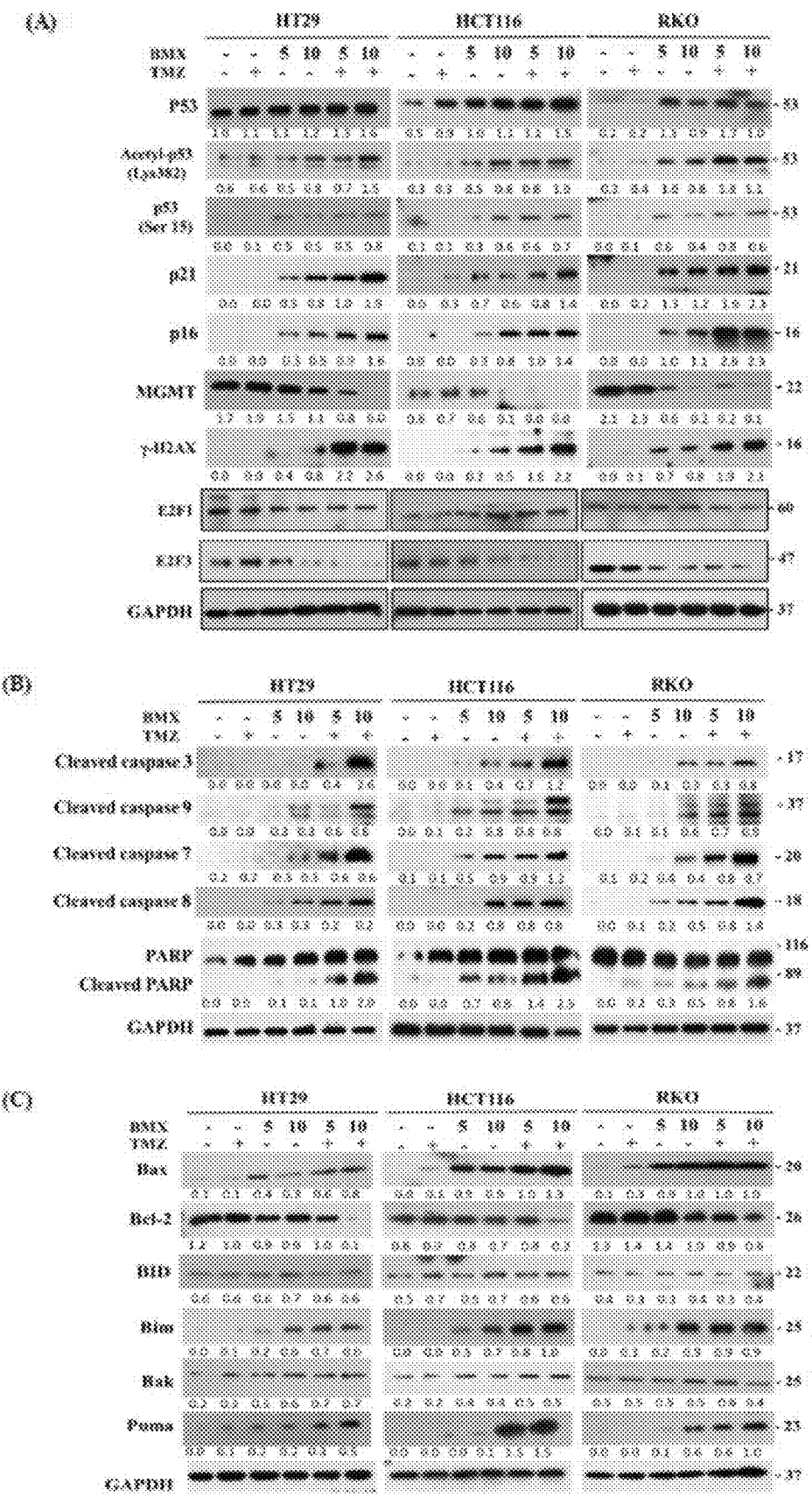

FIG. 14 shows effects of BMX, BMX and TMZ combination-induced apoptosis and autophagy were mediated by p53 mediated MGMT inhibition. (A) Western blot analysis of P53, p53 Lys382 acetylation, p53 Ser15 phosphorylation, p21, p16, MGMT, γH2AX, E2F1 and E2F3 expression in HT29, HCT116 and RKO cells treated with various concentrations BMX (5 and 10 μM) and BMX combined with TMZ for 48 hrs. (B) Expressions of cleaved caspase-3, -7, -8, -9 and cleaved PARP proteins in HT29, HCT116 and RKO cells treated with various concentrations BMX (5 and 10 uM) and BMX combined with TMZ for 48 hrs. (C) Expressions of Bax, Bcl-2, BID, Bim, Bak and Puna proteins in HT29, HCT116 and RKO cells treated with various concentrations BMX (5 and 10 uM) and BMX combined with TMZ for 48 hrs. GAPDH was used as the loading control.

Figure 15:
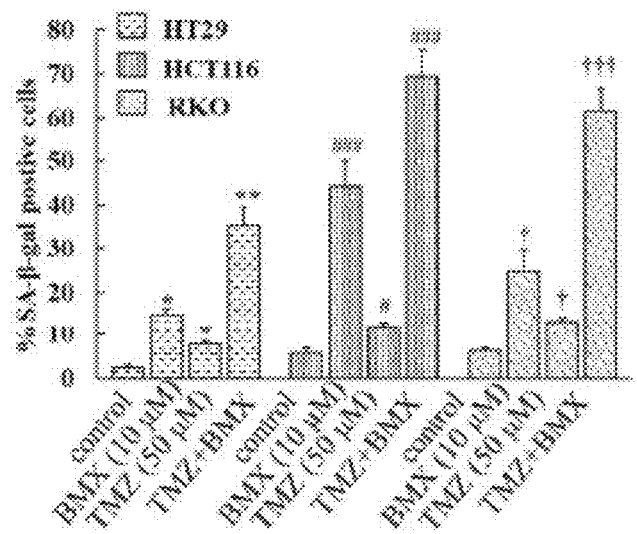

FIG. 15 shows BMX, BMX and TMZ combination induces cellular senescence in HT29, HCT116 and RKO cells. Senescence-associated β-galactosidase (SAβ-gal) staining of BMX and TMZ combination. Cells were treated with 10 μM of BMX plus TMZ (50 μM) for 48 hrs, the cells were stained with SAβ-gal (blue cytoplasmic stain). Scale bar, 50 μm. Quantification of SAβ-gal activity. All results are shown as mean±s.d. from three independent experiments. *p<0.05, p<0.01, *p<0.001 vs. control (HT29 cells); #p<0.05, ##p<0.01, ###p<0.001 vs. control (HCT116 cells); †p<0.05, ††p<0.01, †††p<0.001 vs. control (RKO cells).

Figure 16:
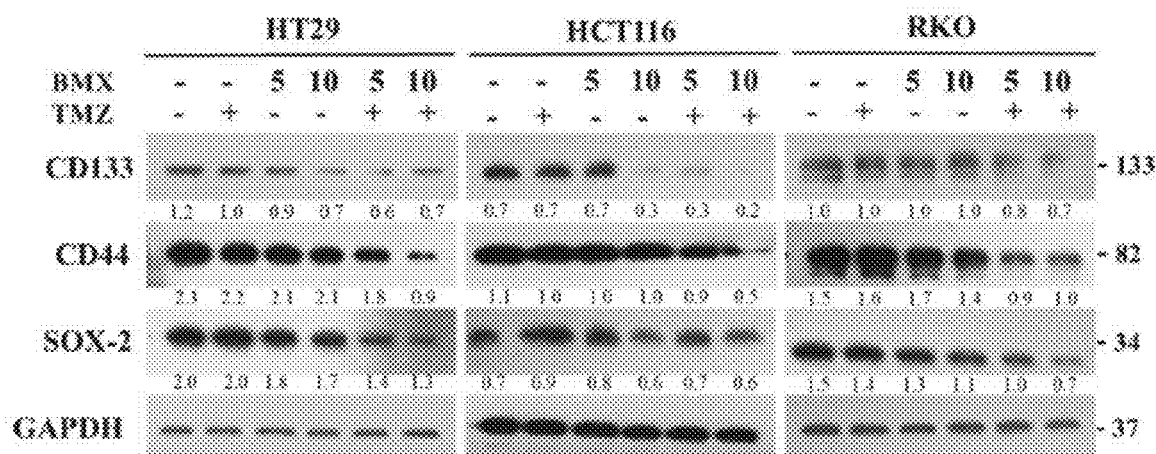

FIG. 16 shows BMX and TMZ combination reduced CSC formation in HT29, HCT116 and RKO cells. Changes in CD133, CD44, and SOX2 protein levels after receiving 5 and 10 μM BMX with or without 50 μM TMZ for 48 hrs on HT29, HCT116 and RKO cells. GAPDH was used as the loading control.

Figure 17:
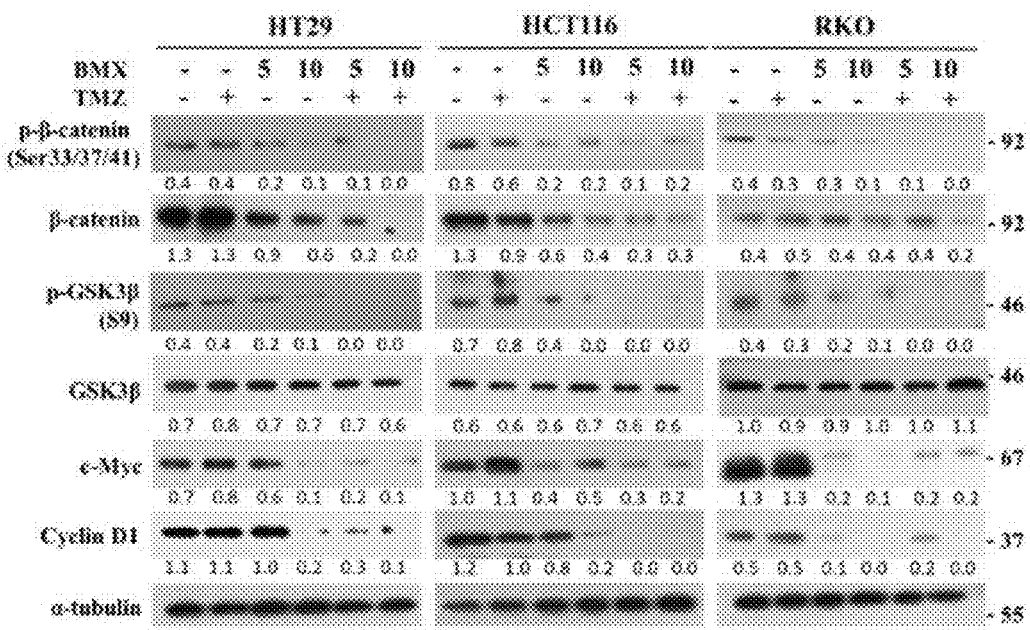
Figure 17:
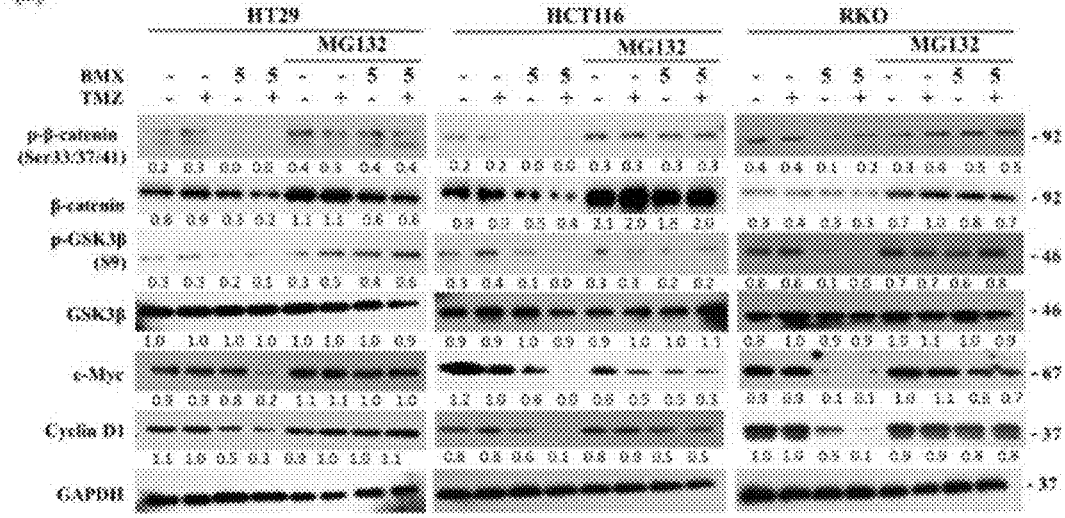
Figure 17:
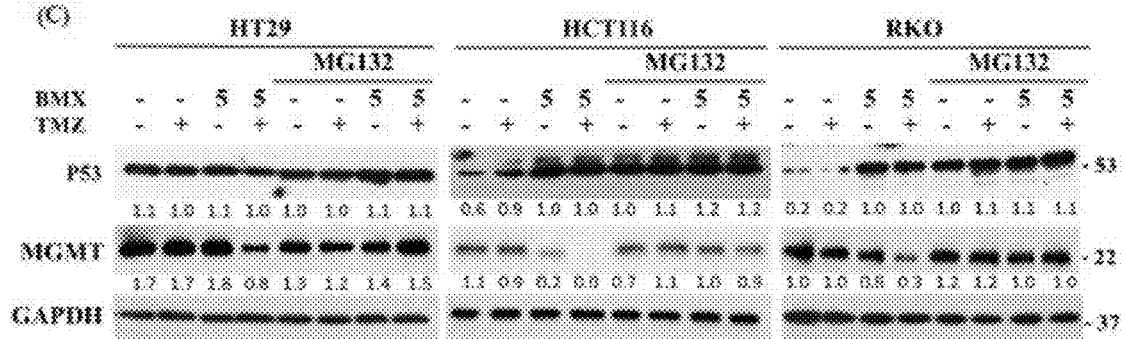

FIG. 17 shows BMX enhanced the TMZ-mediated cytotoxic effect by targeting the Wnt/β-catenin/GSK3β pathway in CRC cells. (A) GSK-3β,β-catenin activation status, c-Myc and Cyclin D1 of HT29, HCT116 and RKO cells after treatment with 5 or 10 μM BMX with or without 50 μM TMZ for 48 hrs. (B) GSK-3β,β-catenin activation status, c-Myc and Cyclin D1 expression is upregulated by BMX with or without 50 μM TMZ and MG132 in T29, HCT116 and RKO cells. (C) P53 and MGMT expression is upregulated by BMX with or without 50 μM TMZ and MG132 in T29, HCT116 and RKO cells. GAPDH was used as the loading control.

FIGS. 18A-18D show autophagy was responsible for BMX along, BMX and TMZ combination induced cell death. (A) LC3 and P62/SQSTM1 expression in HT29, HCT116 and RKO cells treated with BMX (5 and 10 μM) with or without 50 μM TMZ evaluated by western blot. (B) p62/SQSTM1 expression is downregulated by BMX with or without 50 μM TMZ and MG132 in T29, HCT116 and RKO cells. (C) Pre-treatment with BAF and VAD reduced the cell apoptosis in HT29, HCT116 and RKO cells exposed to BMX (5 and 10 μM) with or without 50 μM TMZ for 48 hrs. (D) Effects of VAD and BAF on BMX (5 and 10 μM) with or without 50 μM TMZ induced cleaved caspase-3, cleaved PARP, P62 and LC3 expression. GAPDH was used as the loading control.

DETAILED DESCRIPTION OF THE INVENTION

Unless defined otherwise, all technical and scientific terms used herein have the same meaning as commonly understood by a person skilled in the art to which this invention belongs.

The invention provides a new method for treating a TMZ-resistant cancer (e.g., GBM and CRC) patient is provided using a combination of TMZ and a Compound A.

Compound A is a novel small-molecule isoform-selective HDAC8 inhibitor. The compound A is disclosed in U.S. Pat. No. 7,994,357, the content of which is hereby incorporated by reference in its entirety. The compound A has a structure of Formula A, or a pharmaceutically acceptable salt, stereoisomer, enantiomer, prodrug or solvate thereof:

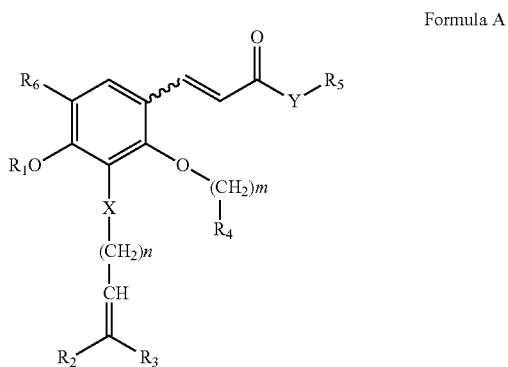

Formula A wherein
$R^1$ is hydrogen, alkyl, alkenyl, $C_5$-$C_6$ cycloalkyl, 5-membered or 6-membered unsaturated carbocycle or 5-membered or 6-membered heterocycle, or $(CH_2)mR^4$;
X is C, —O—, —N— or —S—;
Y is —O—, —NH or —O—$C_1$-$C_4$ alkyl;
n is an integer of 0 to 10;
m is an integer of 0 to 5;
$R^2$ and $R^3$ is independently $C_1$-$C_6$ alkyl;
$R^4$ is $C_5$-$C_6$ cycloalkyl or 5-membered or 6-membered unsaturated carbocycle or heterocycle which may be substituted with halogen, —$CF_3$, —$OR^7$ or —$NR^7R^8$, wherein $R^7$ and $R^8$ are independently hydrogen or $C_1$-$C_6$ alkyl;
$R^5$ is OH, $NH_2$ or C5-C6 cycloalkyl, 5-membered or 6-membered unsaturated carbocycle or heterocycle wherein the cycloalkyl, carbocycle and heterocycle may be optionally substituted with halogen, $NH_2$, $NO_2$, $C_1$-$C_6$ alkoxy, $C_{1-6}$ alkylthio, $OR^{7''}$, $NR^7R^8$ or $CF_3$; and
$R^6$ is H, $C_1$-$C_{10}$ to alkyl which may be substituted by hydroxy or $C_2$-$C_{10}$ to alkenyl, or together with $R_1$ being —$C_2H_2$—.

In one particular embodiment of the present invention, the Compound A is BMX, which was derived from the semi-synthesis of osthole and play a novel role in learning and memory as reported in Yang Y C et al. [22]:

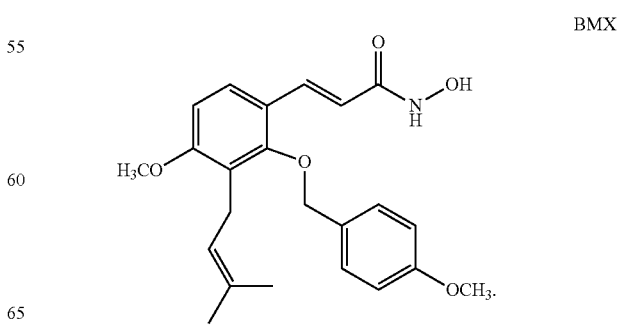

BMX

It is known that BMX is an isoform-selective HDAC8 inhibitor, having the lowest toxicity and the ability to cross the blood-brain barrier[22].

As used herein, the term "Temozolomide" or "TMZ", which is sold under the brand name "Temodar" among others, refers to a medication used to treat some brain tumors such as glioblastoma multiforme or anaplastic astrocytoma. TMZ has the structure below:

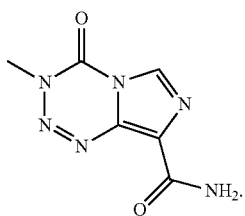

Temozolomide (TMZ) is an alkylating agent used for treatment of some cancers, such as a second-line treatment for astrocytoma and a first-line treatment for glioblastoma multiforme. It is also found that Olaparib in combination with temozolomide demonstrated substantial clinical activity in relapsed small cell lung cancer.

As used herein, the term "glioblastoma multiforme," "glioblastoma" or "GBM" refers to a brain cancer, which can either start from normal brain cells or develop from an existing low-grade astrocytoma. There is no known method of preventing GBM. Treatment usually involves surgery, after which chemotherapy and radiation therapy are used. The medication temozolomide (TMZ) is frequently used as part of chemotherapy.

As used herein, the term "colon cancer," "colorectal cancer" or "CRC" also known as bowel cancer, or rectal cancer, refers to a cancer developed from the colon or rectum (parts of the large intestine). Its signs and symptoms may include blood in the stool, a change in bowel movements, weight loss, and fatigue. The standard treatments of CRC are surgery, radiation and/or chemotherapy, in which Oxaliplatin (Oxp) and its prodrug capecitabine are widely used in clinical practice. Unfortunately, the recurrence under this kind of DNA crosslink agent treatment is still common within the first few years even after completing the whole cycle.

In the present invention, BMX is found to overcome TMZ resistance by enhancing TMZ-mediated cytotoxic effect by downregulating the β-catenin/c-Myc/SOX2 signaling pathway and upregulating WT-p53 mediated MGMT inhibition. The results in the present invention indicated that BMX or its combination with TMZ is promising for precision personal treatment of TMZ-resistant WT-p53 GBM or CRC cells.

The present invention is further illustrated by the following examples, which are provided for the purpose of demonstration rather than limitation.

Example 1

1.1 Materials and Methods
1.1.1 Cell Culture and Reagents

Four GBM cell lines U87, U87R, A172, and A172R were used in this study. The American Type Culture Collection (ATCC; Manassas, Va., USA) provided human GBM cell lines U87-MG (ATCC HTB-14; GBM of unknown origin) and A172 (ATCC CRL-1620; ATCC). U87R and A172R cells were obtained from Dr. Tsung-I Hsu and Dr. Jian-Ying Chung (The Ph.D. Program for Neural Regenerative Medicine, College of Medical Science and Technology, Taipei Medical University, Taipei, Taiwan). These cells were maintained in Dulbecco's modified Eagle medium (DMEM) with 10% fetal bovine serum (FBS) and 50 μM TMZ for at least 60 days. TMZ resistance in U87R and A172R cells was confirmed using the colony formation assay (FIG. 11). Cells were cultured in DMEM supplemented with 10% FBS, 100 U/mL penicillin, 100 mg/mL streptomycin (all from Gibco; Thermo Fisher Scientific, Waltham, Mass., USA) and maintained in a humidified incubator at 37° C. and 5% $CO_2$. NBM-BMX (BMX), (E)-2-(4-Methoxybenzyloxy)-3-prenyl-4-methoxy-N-hydroxycinamide, was provided by NatureWise Biotech & Medicals Corporation (Taipei, Taiwan).

1.1.2 Cell Proliferation and Colony Formation Assays

We plated 3000 GBM cells per well in 96-well plates and allowed them to adhere overnight. To validate cell line responsiveness to BMX and TMZ monotherapy, the cells were treated with different doses of BMX or TMZ for 24, 48, and 72 hrs. To confirm cell responsiveness to the BMX-TMZ combination, cells were either treated with different doses of TMZ (0-800 μg/mL) with or without BMX (10 μM) for 24, 48, and 72 hrs or with different doses of BMX (0-50 μM) with or without TMZ (50 μM) for 24, 48, and 72 hrs. Following treatment, the absorption value was measured using a CCK8 kit (Targetmol, Shanghai, China) at the indicated time points. The results are reported as the mean±standard deviation of at least three replicates.

A172, A172-R, U87MG, and U87MG-R cells were seeded (1000 cells/dish) into 6-cm culture dishes and incubated for 14 days. The cells were washed three times with phosphate-buffered saline, fixed in 4% paraformaldehyde for 30 min, and stained with 0.1% crystal violet for 20 min at 25° C. The colonies were carefully washed with tap water, and then the number of colonies, defined as at least 50 cells, were counted and analyzed. The results are expressed as the average colony count±SE from three independent experiments.

0.1.3 Reverse Transcription-Quantitative Polymerase Chain Reaction (RT-qPCR)

The ABI Prism® 7700 Sequence Detection System (Applied Biosystems, Foster City, Calif., USA) was used for quantitative analysis of mRNA expression. The cells ($2\times10^5$) were seeded in 6-well plates, and total RNA was extracted using Tissue Total RNA Mini Kit (Geneaid, Taipei, Taiwan). A 10-ng sample of total RNA was transcribed into cDNA by using a High-Capacity cDNA Reverse Transcription Kit (Applied Biosystems). Gene expression was quantified using Fast SYBR Green Master Mix (Applied Biosystems) following the procedures provided by the manufacturer, with 18s as the inner reference. All procedures were performed according to the manufacturer's protocols. The thermocycling conditions were as follows: 50° C. for 2 min, 95° C. for 10 min, and 40 cycles of 95° C. for 15 s and 60° C. for 1 s. Each sample was analyzed in triplicate. The threshold cycle (Ct) values were calculated using the StepOnePlus (Applied Biosystems) software. The relative expression of each mRNA was calculated using the 2-(ΔCt) method. The primer sequences for HDAC8 were as follows:

```
HDAC8 forward
                                (SEQ ID NO: 1)
5'-GCGTGATTTCCAGCACATAA-3';

HDAC8 reverse
                                (SEQ ID NO: 2)
5'-ATACTTGACCGGGGTCATCC-3'.

18s forward
                                (SEQ ID NO: 3)
5'-TCAAGTGCAGTGCAACAACTC-3';

18s reverse
                                (SEQ ID NO: 4)
5'-AGAGGACAGGGTGGAGTAATCA-3'.
```

1.1.4 Flow Cytometric Analysis of the DNA Cell Cycle

For the DNA cell cycle, following treatment with different doses of BMX (0-10 μM) in the presence or absence of TMZ (50 μM) for 48 hrs, the cells were harvested through trypsinization, washed twice with phosphate-buffered saline, and fixed in methanol. The cells were then washed again, subjected to RNase A at a final concentration of 0.05 mg/mL (Sigma-Aldrich; Merck Millipore, Darmstadt, Germany), and incubated with 10 μg/mL propidium iodide (PI; Sigma-Aldrich; Merck Millipore) at 4° C. for 15 min in the dark. Cell cycle analysis was conducted using a fluorescence-activated cell sorting (FACS) flow cytometer (Attune NxT flow cytometer, Thermo Fisher Scientific).

1.1.5 Flow Cytometric Analysis of Apoptosis

To analyze cell apoptosis in different doses of BMX (0-10 μM) in the presence or absence of TMZ (50 μM), FITC-labeled annexin V/PI staining was performed using the CF®488A Annexin V and PI Apoptosis Kit (Fremont, Calif., USA), according to the manufacturer's instructions. The analysis by flow cytometry of PI and annexin was performed 48 hrs post-treatment. A total of 10,000 nuclei were measured using an FACS flow cytometer (Attune NxT flow cytometer, Thermo Fisher Scientific).

1.1.6 Immunohistochemical Staining

Immunohistochemical staining was performed on 4-μm-thick paraffin sections. The sections were dewaxed hydrated and placed at 4° C. overnight. For antibodies against CD133 (AP1802a, Abgent, San Diego, Calif., USA), P62 (ab56416, Abcam, Cambridge, Mass., USA), and LC3II (AP1802a, Abgent), the standard avidin-biotin complex procedures were employed. After the sections were returned to room temperature, biotinylated secondary antibodies and horseradish-labeled streptavidin were added. The samples were then incubated in an oven at 37° C. Subsequently, DAB color development, hematoxylin counterstaining, gradient alcohol dehydration, and xylene transparent were conducted. All samples were sealed with neutral gum afterwards. Human brain tissues: The ethics statements in this study were approved by the Institutional Review Board of Kaohsiung Medical University Hospital (No. KMUHIRB-F(I)-20200024). Informed consent was obtained from all subjects involved in the study.

1.1.7 Western Blot Analysis

The cells were collected and lysed in RIPA lysis buffer (EMD Millipore Billerica, Mass., USA, 10×RIPA buffer) containing a protease inhibitor. Protein concentration was determined using a protein assay kit (Bio-Rad Laboratories, Hercules, Calif., USA). The SDS loading buffer was mixed with the protein samples. Proteins (20 μg/lane) were separated using 8%-12% SDS-PAGE and transferred to a PVDF membrane, which was blocked with 5% bovine serum albumin at room temperature for 1 hr in tris-buffered saline (TBS)-Tween 20 (0.5%; TBS-T), incubated with primary antibodies overnight at 44° C., and then incubated with horseradish peroxidase (HRP)-conjugated secondary antibodies at room temperature for 1 hr. After washing thoroughly with TBS-T, the HRP signals were detected with a chemical HRP substrate. The antibodies we used are listed in Table 3. Signal of each target protein was visualized by incubation with an enhanced chemiluminescent reagent and exposure to X-ray film.

1.1.8 Statistical Analysis

Data are presented as mean±standard deviation. Statistical analyses were performed using one-way analysis of variance. Data were compared using the Student's t test. The level of statistical significance was set at *$p<0.05$, $p<0.01$, *$p<0.001$.

TABLE 3

Experimental antibodies.

| Designation | Source or Reference | Identifiers | Additional Information |
|---|---|---|---|
| GAPDH | Arigo, Hsinchu, Taiwan | ARG10112 | 1:5000 |
| β-actin | Santa Cruz, CA, USA | sc-47778 | 1:2000 |
| HDAC8 | ABclonal, Woburn, MA, USA | A8865 | 1:1000 |
| c-Myc | Cell Signaling Technology, Inc | #5605s | 1:1000 |
| cyclin D1 | Cell Signaling Technology, Inc | #2978s | 1:1000 |
| cyclin B | Cell Signaling Technology, Inc | #12231s | 1:1000 |
| Caspase-3 | p15; | NB100-56708 | 1:1000 |
| Bax | Cell Signaling Technology, Inc | #2772s | 1:1000 |
| p21 | Cell Signaling Technology, Inc | #2947s | 1:1000 |
| Bcl-xL | Cell Signaling Technology, Inc | #2764s | 1:1000 |
| phospho-p53 | p15; | #9284s | 1:1000 |
| puma | Cell Signaling Technology, Inc | #12450s | 1:1000 |
| MGMT | Cell Signaling Technology, Inc | #2739s | 1:1000 |
| p53 | Santa Cruz, CA, USA | sc-126 | 1:1000 |
| CD133 | Cell Signaling Technology, Inc | #5860s | 1:1000 |
| CD44 | Abcam, Cambridge, MA, USA | ab157107 | 1:1000 |
| SOX-2 | Cell Signaling Technology, Inc | ab97959 | 1:1000 |

1.1.9 Predict the Potential Mechanism of a HDAC8 Inhibitor Through Multi-Database Platform Indirect process: CLUE calculated the connectivity score of shRNA HDAC8 among their one million profiles and ordered the similarity to opposite compounds as well as gene perturbations. The criteria were filtered above 90 positive scores and collected each instance targeted-genes as shRNA HDAC8 regulators in biological function. Input this genes list in CPDB platform for enrichment analysis to obtain clear pathways information. Direct process: Based on BMX-L1000 gene expression data, both up-regulation and down-regulation gene list which respond to the drug biological function in HepG2 cells. BMX (1 μM) compared to DMSO control to define the significant differential expression genes (DEGs) according to ±1.5 fold change, p-value<0.05. Hence, the DEGs were used as inputs to query CPDB for pathway analysis. To narrow down the prioritized pathways, we interested two results and selected the common element.

1.2 Results:

1.2.1. Pathway Analysis for Potential Expression Profile of HDAC8 Inhibitor Through Bioinformatics Tools To explore possible mechanisms of HDAC8 inhibitor and gene involvement, we used Connectivity map (C-Map) and the Library of Integrated Network-Based Cellular Signatures Unified Environment (CLUE) systemic database (https://clue.io/) and ConsensusPathDB (CPDB) platform (http://cpdb.molgen.mpg.de/) for the comprehensive mechanism analysis. We utilized two bioinformatics processes, direct and indirect analyses, respectively (FIG. 1A). For the direct analysis, HepG2 cells were treated with BMX in L1000 plate, which responded to the biological function of BMX (FIG. 1A, right). The significant differentially expressed genes (1583 up-regulation and 900 down-regulation) with 1.5-fold change were used to query the CPDB platform to reveal the potential pathways (p-value<0.05). Next, we analyzed the HDAC8 inhibition function through an indirective approach, pattern matching algorithm of the CLUE platform. Using shRNA HDAC8 signature as the simulation of BMX treatment (HDAC8 inhibitor), we then accessed CLUE, which computed over 1 million profiles to match the similar signature-pattern from 19,811 small molecule compounds or gene perturbations (e.g., 18,493 shRNAs, 3,462 over-expression constructs), and then obtained the connectivity score. The positive score denoted a similar mechanism between query and instance signatures; while the negative meant the opposite function. Our criteria were selected above 90 connectivity scores of compounds (CPs), knockdown genes (KDs), overexpression genes (OE), and perturbagen class (PCLs). CLUE clustered the similar function compounds or same family genes into a particular group which could postulate as the mechanism of action. However, this big data system did not offer detailed pathway information. Thus, we combined the CPDB platform for complementary analysis from shHDAC8 and BMX-treated cells (FIG. 1A, left). These different bioinformatics pipelines would obtain several mechanisms/pathways and we intersected these two datasets to filter the possible potential pathways. Wnt signaling pathway is one of the top-ranking mechanisms uncovered via our multi-databases platform (FIG. 1 B).

0.2.2 BMX Enhanced the TMZ-Mediated Cytotoxic Effect to Inhibit the Growth and Proliferation in GBM-R Cells To investigate whether HDAC8 is correlated with therapy-resistant GBM, we examined the HDAC8 expression level of two parent GBM cell lines (A172 and U87MG, A172 and U87MG are wild-type p53 (WT-p53), FIG. 12) and two TMZ-resistant GBM cell lines (A172-R and U87MG-R, variants of WT-p53). HDAC8 overexpression was detected in both GBM-R cell lines (FIGS. 8A and 8B).

In the example, NBM-BMX (provided by Nature Wise Biotech & Medicals Corporation; BMX was used in this manuscript) was used as a HDAC8 inhibitor to mimic the effect of shRNA HDAC8 for further experiment. The structure of BMX (397.46 Da) is shown in FIG. 2A. It was confirmed that BMX is a HDAC8 inhibitor by treating the four cell lines with BMX and detecting BMX-induced inhibition of HDAC8 mRNA and protein expression (FIGS. 9A and 9B).

Figure 10A:
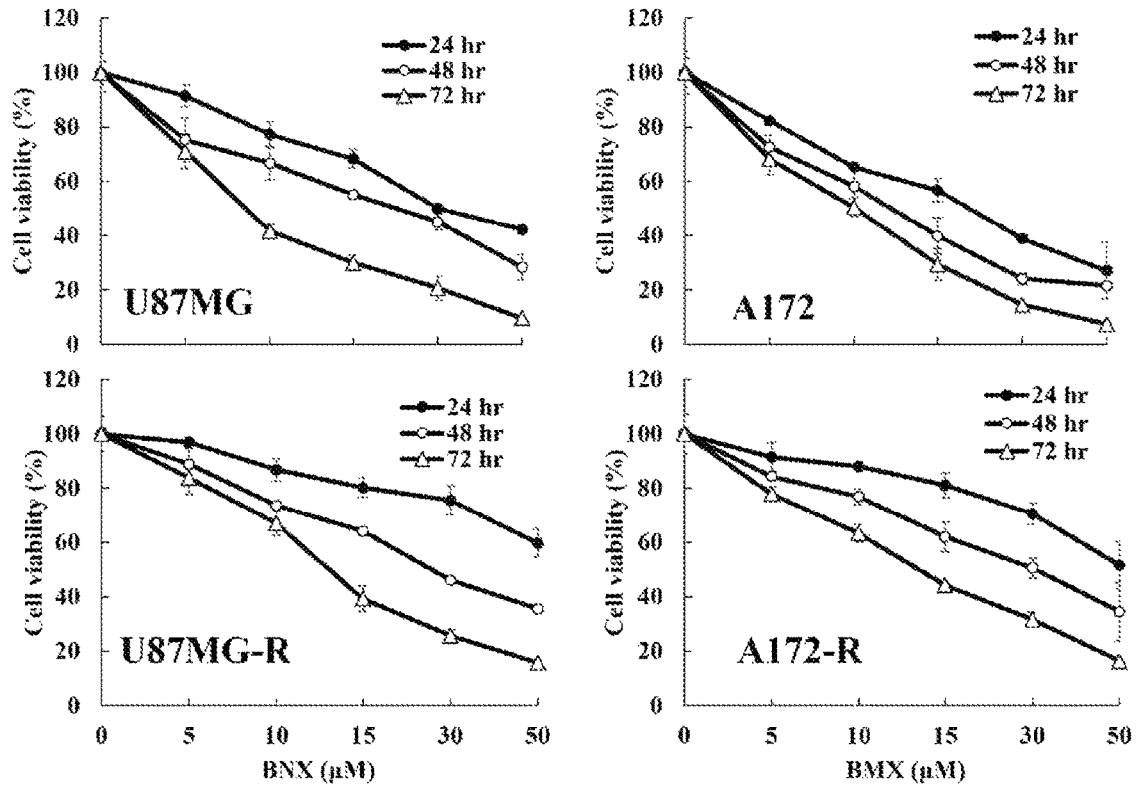
Figure 10B:
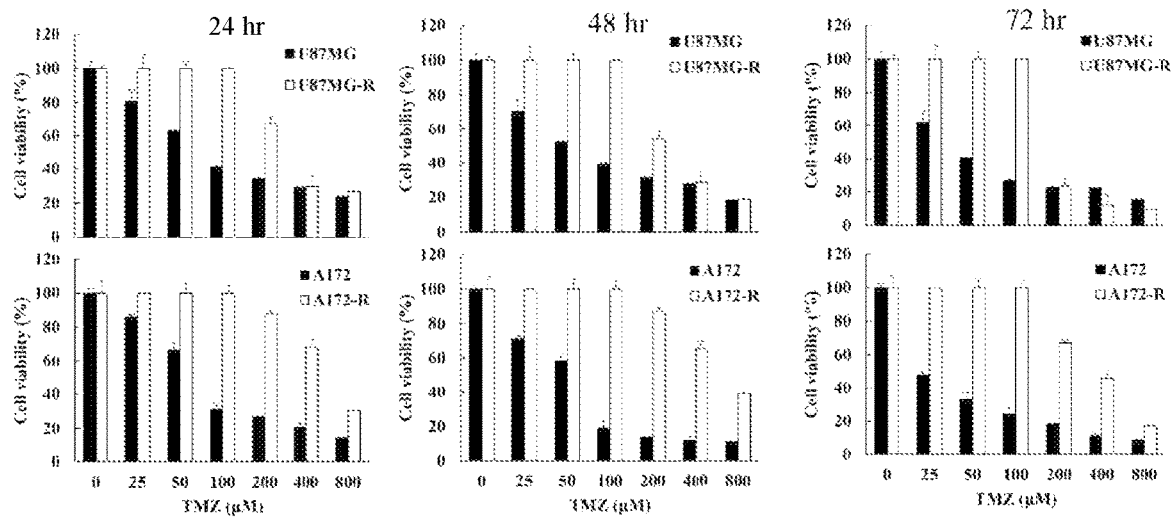
Figure 10C:
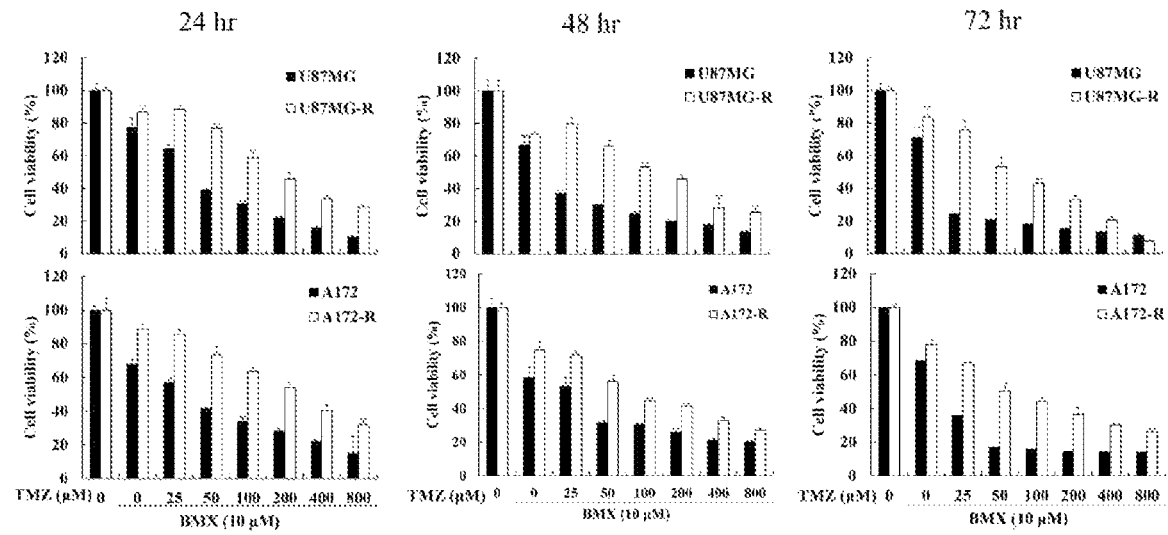
Figure 10D:
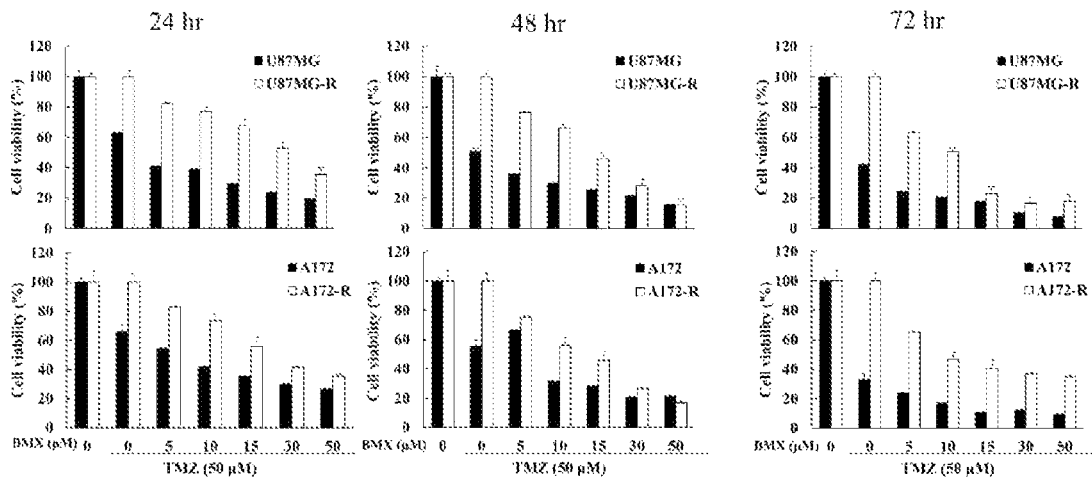

It is believed that BMX might enhance the sensitivity of TMZ-mediated cytotoxic effect in both GBM and GBM-R cells. In this example, it was found that a combination effect exists between BMX and TMZ in treating GBM and GBM-R, in A172/A172-R and U87MG/U87MG-R cells. An MTT assay was performed to assess cell proliferation and cell viability for the BMX-alone, TMZ-alone, and combination groups under different concentrations at 24, 48 and 72 hrs. In each treatment alone group, the results suggested that the cytotoxic effect in each group increased in a time-dependent manner (FIG. 10A). The results revealed that the $IC_{50}$ values of BMX alone were 21.00±2.34 µM/>52.64±3.62 µM in A172/A172-R cells and 29.84±2.32 µM/>68.13±4.69 µM in U87MG/U87MG-R cells (FIG. 2B), suggesting that BMX alone could inhibit GBM cell proliferation, but not inhibit GBM-R cell proliferation. In addition, the $IC_{50}$ values of TMZ alone were 73.48±3.65 µM/80.99±1.68 µM in A172/U87MG cells and 595.07±23.42 µM/302.51±15.24 µM in A172-R/U87MG-R cells, confirming the reliability of GBM-R cells (FIG. 2C). In the combination treatment group, BMX 10 µM was used to combine with different dose of TMZ (FIG. 2D) and TMZ 50 µM (the same as the maintenance concentration in GBM-R cell lines) combined with different concentrations of BMX (FIG. 2E) to determine which dose of BMX and TMZ that can most enhance TMZ-mediated cytotoxic effect in GBM-R cells. The data revealed that 50 µM TMZ with 10 µM BMX exerted the highest cytotoxic effect in both GBM-R cell lines. We used this combination in a time-dependent manner and noted a cytotoxic effect in 48 hrs (FIG. 2F, in 48 hrs BMX10 µM: 0.88×, 0.77×, 0.63×; BMX and TMZ: 0.74×, 0.56×, 0.47×). The clonogenic assay also revealed that 10 µM BMX with 50 µM TMZ, rather than BMX alone, suppressed GBM-R cells (FIG. 2G). In view of the abovey, the data suggest that the combination treatment inhibits the growth and proliferation of GBM cells (U87MG and A172) and GBM-R cells (U87MG-R and A172-R), and the combination of 10 µM BMX and 50 µM TMZ exerts the highest cytotoxic effect (suppression of cell proliferation and cell viability) on GBM-R cells. Nevertheless, the cell viability of BMX alone was still moderately decreased to show the partial ability of pharmacological cytotoxic effect in A172R/U87R, comparing with TMZ alone with no suppression effect. Thus, the combined BMX and TMZ treatment was compared with BMX alone in the further experiments.

1.2.3 BMX enhanced the TMZ-mediated cytotoxic effect by targeting the Wnt/β-catenin/GSK3β pathway in GBM-R cells The mechanism was investigated by the enhancement of in the TMZ-mediated cytotoxic effect in GBM-R cells. On the basis of the pathway analysis, it was postulated that the canonical Wnt signaling (also known as Wnt/β-catenin) pathway was involved in the proliferation of GBM-R cells. The genetic background for each cell indicated no mutation in Wnt genes, such as adenomatous polyposis coli and β-catenin (CTNNB1). The phospho-β-catenin (Ser33/Ser37/Thr41) as a β-catenin active form for detecting the β-catenin status. GSK3β (S9) was used for β-catenin phosphorylation to degrade β-catenin. The results indicated that 10 µM BMX with 50 µM TMZ reduced the protein levels of β-catenin directly and reduced the protein levels of phospho-β-catenin (Ser33/Ser37/Thr41) through phosphorylation by GSK3β in U87R and A172R cells, whereas BMX alone only slightly reduced these levels. Moreover, the phosphorylation level of GSK3β (S9) also decreased, indicating that GSK3β activity increased and β-catenin was phosphorylated (FIG. 3A). To examine the effects of BMX on the proliferative markers c-Myc and cyclin D1, it was noted that BMX both with and without TMZ could decrease their levels (FIG. 3B).

The GBM-R cells were treated with the proteasome inhibitor MG132 to verify that the β-catenin protein level decreased due to protein degradation. The results revealed that MG132 application reversed β-catenin degradation and increased c-Myc and cyclin D1 expression under 10 μM BMX and 50 μM TMZ (FIG. 3C). These results demonstrated that BMX enhanced GSK3β activity through Ser9 phosphorylation downregulation, which in turn enhanced β-catenin phosphorylation at Ser33/Ser37/Thr41, triggering protein degradation. Taken together, these data revealed that 10 μM BMX and 50 μM TMZ enhanced TMZ-mediated cytotoxic effects, partly via the Wnt/β-catenin/GSK3β pathway, thus reducing GBM-R cell proliferation.

Figure 4A:
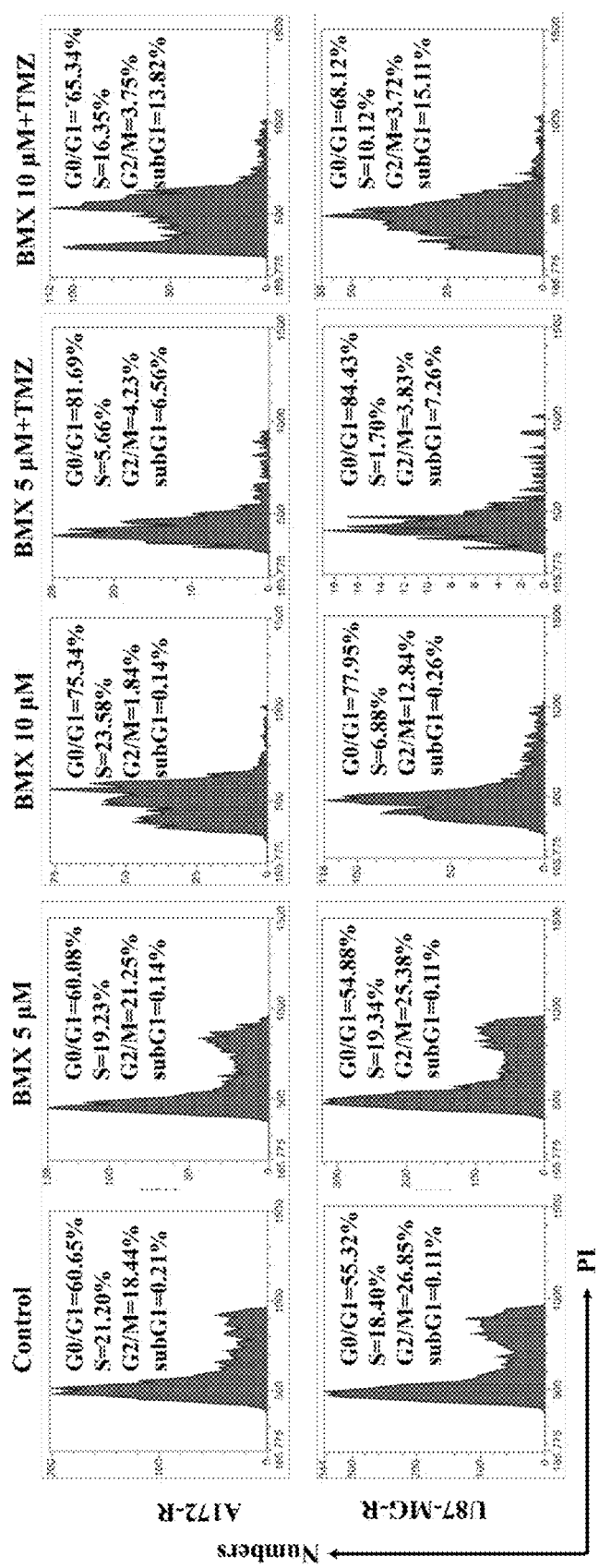
Figure 4B:
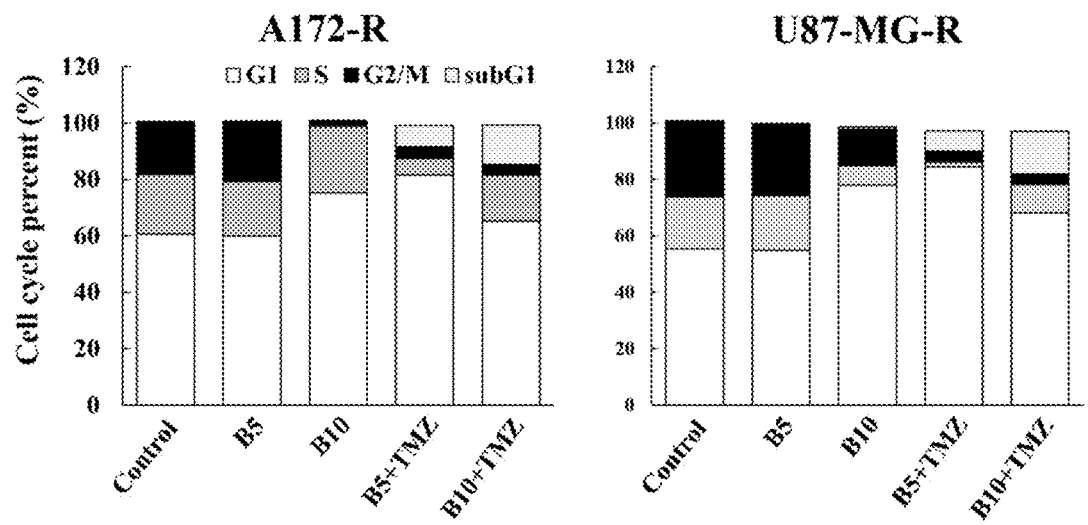
Figure 4C:
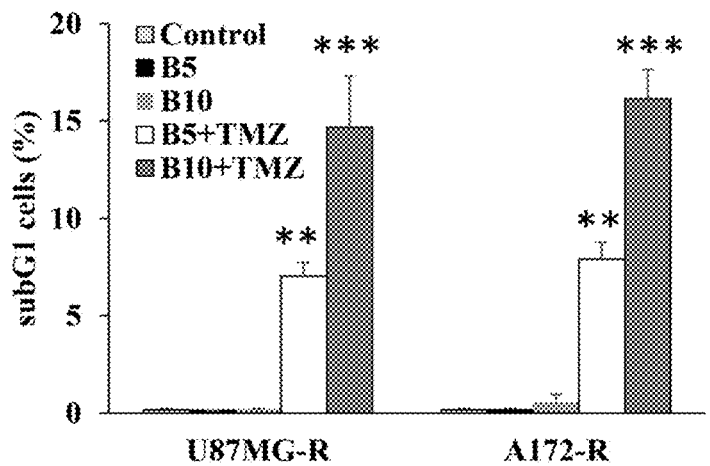

1.2.4 BMX Enhanced the TMZ-Mediated Cytotoxic Effect by Promoting TMZ-Mediated Apoptosis in GBM-R Cells To investigate whether BMX can induce cell cycle arrest, it was analyzed the effects of BMX (5 μM and 10 μM) alone and combined with 50 μM TMZ on the cell cycle in the A172-R and U87MG-R cell lines. The results revealed that 10 μM BMX alone induced cell cycle arrest in the G0/G1 phase in A172-R cells (70.34%) and U87MG-R cells (77.95%). Next, 5 and 10 μM BMX with 50 μM TMZ not only increased the amount of cell cycle arrest in G0/G1 but also caused arrest in the sub-G1 phase (apoptosis) in both GBM-R cell lines (FIG. 4A-C).

Figure 4D:
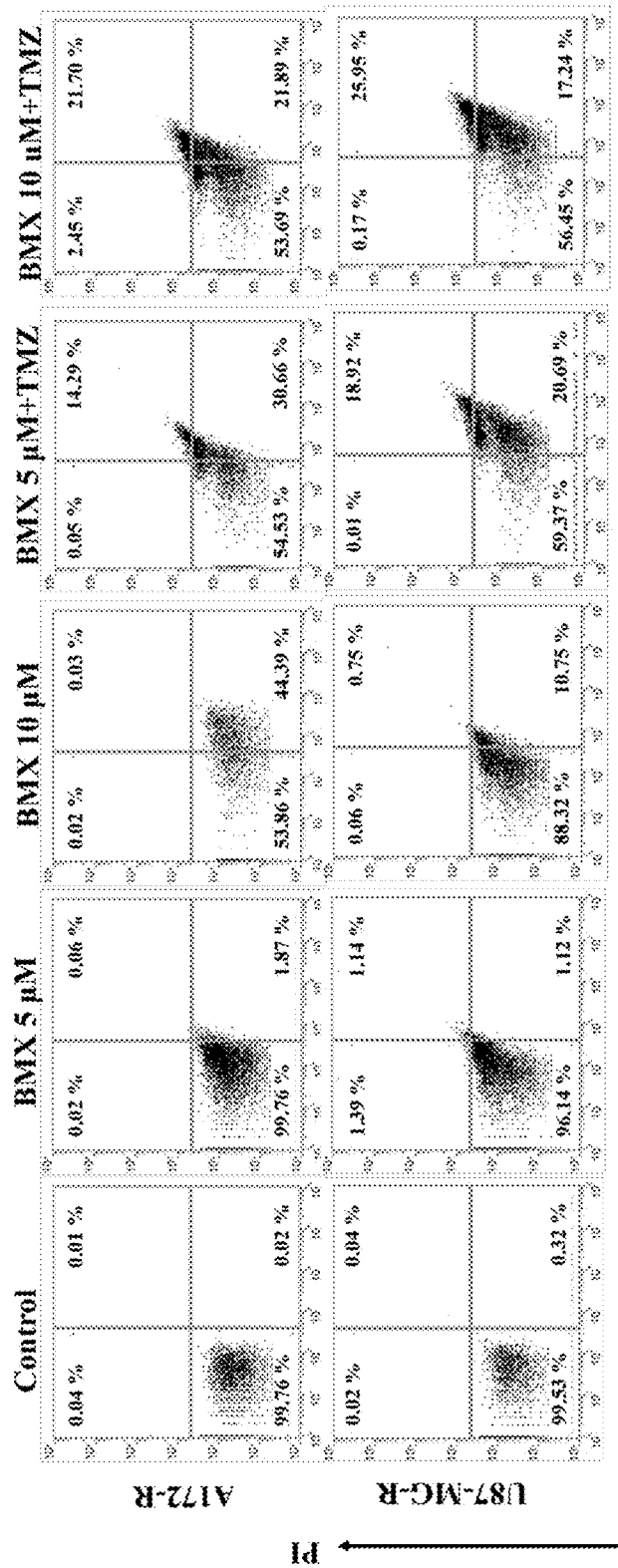
Figure 4E:
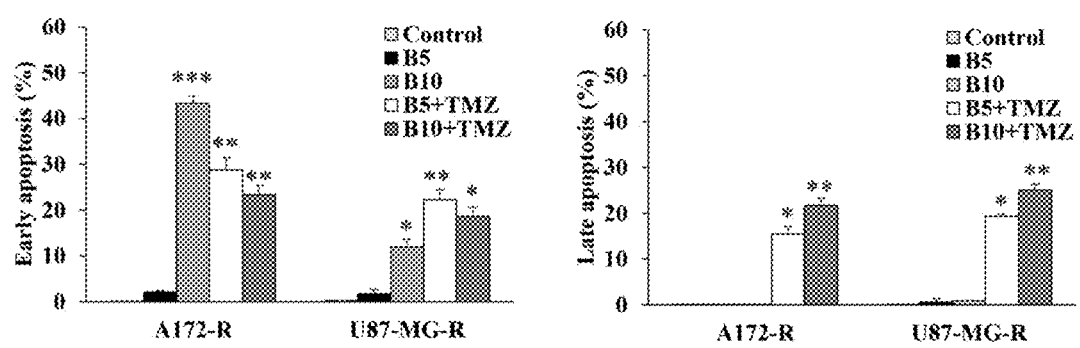

Flow cytometry revealed that BMX combined with TMZ yielded a high percentage of apoptotic cells in A172-R/U87MG-R cell lines (21.7%/25.95%) in a dose-dependent manner (FIG. 4D). Moreover, late apoptosis was also predominant after treatment with 10 μM BMX and 50 μM TMZ (FIG. 4E). Thus, BMX alone could only induce cell cycle arrest and suppress cell proliferation but not induce apoptosis, whereas the BMX and TMZ combination could also promote TMZ-mediated apoptosis, leading to enhanced cytotoxicity, in GBM-R cells.

1.2.5 BMX Enhanced the TMZ-Mediated Cytotoxic Effects by WT-p53 Mediated MGMT Inhibition in GBM-R Cells Because the BMX and TMZ combination could promote TMZ-mediated apoptosis, we speculated that BMX might enhance TMZ-mediated apoptosis through WT-p53 mediated MGMT inhibition. First, we examined WT-p53 and MGMT levels in A172/A172-R and U87MG/U87MG-R cells, confirming that TMZ resistance is related to WT-p53 and MGMT (FIG. 5A). The bioinformatics analysis also suggested that only 33% patients have p53 mutation, others are p53 WT (Table 2). Next, the TCGA and driverDB databases were assessed to check the overall survival rate between p53 mutation and p53 WT. By colony formation assay (FIG. 11), it was clearly revealed that p53 WT cases showed poor prognosis in GBM patients as compared to the mutated cases.

We examined the proapoptotic signaling system in WT-p53 mediated apoptosis. MGMT was also examined for TMZ repair ability. The results revealed that the levels of proapoptotic makers, such as P21, Bax/Bcl2, and Puma, increased and that those of MGMT decreased after treatment with BMX both without and with 50 μM TMZ. However, cleaved caspase-3 was only noted with the combination of 10 μM BMX and 50 μM TMZ (FIG. 5B). To clarify whether apoptosis is induced by BMX alone, TMZ alone, or their combination in WT-p53 mediated MGMT inhibition, A172-R and U87MG-R cells were treated with 50 μM TMZ without or with 5 and 10 μM BMX. It was found that TMZ alone could only moderately suppress MGMT expression without increasing WT-p53 and DNA damage marker (WT-p53-ser15). However, MGMT expression obviously decreased with the combination of 10 μM BMX and 50 μM TMZ. Moreover, WT-p53 and DNA damage markers (WT-p53-ser15) expression levels also increased, meaning that MGMT was negatively regulated by WT-p53 mediated apoptosis (FIG. 5C).

Moreover, by assessing scatter plot for p53 WT and mutant cells (FIG. 8B), it was found that GBM p53 WT cells were MGMT hypermethylated and lower the MGMT mRNA and protein expression as well. In addition, TMZ alone could not induce WT-p53 mediated apoptosis in GBM-R cells. However, these data suggested that BMX and TMZ combination could enhance the TMZ-mediated cytotoxic effect through WT-p53 mediated MGMT inhibition in GBM-R cells. BMX alone could moderately decrease MGMT levels but not induce WT-p53 mediated apoptosis in GBM-R cells.

TABLE 2

| CCLE p53 genetic features | | | |
|---|---|---|---|
| Tp53-WT | | Tp53-mut | |
| SF126 | KS1 | LN229 | YKG1 |
| BECKER | MOGGUVW | SW1783 | X8MGBA |
| GOS3 | U87MG | TM31 | MOGGCCM |
| KNS81 | LN443 | U138MG | |
| KG1C | LN235 | SF295 | |
| AM38 | SF172 | M059K | |
| H4 | U343 | GI1 | |
| D283MED | U178 | KNS60 | |
| NMCG1 | F5 | KALS1 | |
| YH13 | SF767 | CAS1 | |
| DKMG | A1207 | KNS42 | |
| U118MG | LN319 | SNU201 | |
| GB1 | LN382 | SNU1105 | |
| SNU489 | LNZ308 | SNU738 | |
| SNU466 | LN340 | SNU626 | |
| CCFSTTG1 | CH157MN | DAOY | |
| D341MED | SF268 | SW1088 | |
| ONS76 | SF539 | HS683 | |
| DBTRG05MG | SNB75 | LN18 | |
| A172 | | T98G | |
| X132N1 | | GMS10 | |
| SNB19 | | X42MGBA | |
| U251MG | | GAMG | |

1.2.6 The Combination of BMX and TMZ Reduced GSC Formation in GBM-R Cells

Because GSC markers are the core of GBM resistance, we examined the levels of GSC markers in all cell lines; high expression levels of CD133, CD44, and SOX2 were detected in A172-R and U87MG-R cells, implying that TMZ resistance is partly related to GSC markers (FIG. 6A). Furthermore, treatment with 10 μM BMX and 50 μM TMZ clearly reduced the expression levels of CD133, CD44, and SOX2 in both GBM-R cell lines (FIG. 6B). Thus, the BMX and TMZ combination could enhance the TMZ-mediated cytotoxic effect by attenuating GSC markers to convert the stemness phenotype in GBM-R cells.

We also examined HDAC8 and GSC markers in TMZ-resistant GBM human tissues through immunohistochemistry (FIG. 6C). The results revealed that HDAC8 and GSC are closely related to TMZ resistance in GBM.

1.3. Conclusion

Although preclinical studies have indicated that HDAC is have antitumor effects in glioma, none of the previous studies mentioned or expected the treatment of chemotherapy-resistant GBM. It was first found in the present invention that BMX, a novel iso-selective HDAC8 inhibitor, can enhance TMZ-mediated cytotoxic effect not only by downregulating the β-catenin/c-Myc/SOX2 pathway to inhibit stemness, but also by upregulating WT-p53 mediated MGMT inhibition to induce apoptosis in TMZ-resistant GBM cells. Moreover, it was also revealed that the inverse correlation of WT-p53/MGMT reversion and the Wnt/β-catenin/GSKβ signaling pathway may be involved in the oncogenic role in GBM and GBM with TMZ resistance.

Based on the above-mentioned results, the following working model is proposed (see FIG. 7):

First, β-catenin/c-Myc/cyclin D1/SOX2 signaling pathway in TMZ-resistant GBM (Pathway in right side). According to our previous studies and the bioinformatics analysis in this study, the Wnt/β-catenin/GSK3β pathway can influence therapy selection for GBM [17]. It was demonstrated in the present invention that both of BMX without and with TMZ (thin and thick lines) could enhance GSK3β activity by downregulating Ser9 phosphorylation, which in turn enhanced β-catenin phosphorylation at Ser33/Ser37/Thr41, triggering β-catenin protein degradation. β-catenin degradation was confirmed with MG132 as a proteasome inhibitor. Undegraded β-catenin translocates into the nucleus to bind to TCL4 and activate downstream target genes, such as c-Myc and cyclin D1, to induce cell proliferation and continue the cell cycle. Both BMX alone (thin lines) and BMX with TMZ (thick lines) suppressed c-Myc and cyclin D1 expression and induced cell cycle arrest. However, BMX alone could not induce cell cycle arrest in the sub-G1 phase. Only the combination of BMX and TMZ induced profound cell cycle arrest and proceeded to the sub-G1 phase, meaning that it induced late-apoptosis in GBM-R cells (dotted line in the right lower part in FIG. 7).

In addition, GSCs play a vital role in therapeutic resistance in GBM. They are characterized by their self-renewal ability, both in vitro and in vivo, through high expressions of neuronal stem cell markers, such as CD133 and CD44, as well as transcription factors, such as SOX2 [23]. It was revealed in the invention that BMX both without and with TMZ attenuated not only CD133 and CD44 but also SOX2 by downregulating the GSC phenotype to suppress sternness. As previously reported, c-Myc is also required to maintain glioma CSCs [24]. It could be concluded that BMX alone and BMX with TMZ suppressed cell proliferation by enhancing the TMZ-mediated cytotoxic effect via the β-catenin/c-Myc/cyclin D1/SOX2 signaling pathway in GBM-R cells.

Furthermore, WT-p53 mediated MGMT inhibition in TMZ-resistant GBM (Pathway in left side in FIG. 7). The mechanism of action of TMZ in GBM is methylation of the O6 position to guanine to damage DNA. MGMT reverses methylation to repair DNA in GBM cells and to exert GBM resistance. Although an MGMT-independent pathway also plays a critical role in TMZ resistance[25-27], the MGMT-dependent pathway is still considered the major pathway for TMZ resistance. In the present invention, GBM-R cell lines (A172-R and U87MG-R) expressed high levels of the MGMT protein, thus verifying that the MGMT-dependent pathway is indeed a major mechanism for TMZ resistance in these cell lines. It may be speculated that BMX suppressed MGMT expression in MGMT-dependent GBM-R cell lines to weaken the ability of MGMT for DNA damage repair. In the GBM-R cell lines, BMX alone moderately decreased MGMT expression and TMZ alone did not (FIG. 5B and FIG. 5C), but their combination obviously reduced the MGMT protein levels and enhanced TMZ-mediated apoptosis in an MGMT-dependent manner.

As shown in FIG. 7, the model includes two main signaling pathways. The pathway on the right side: β-catenin/c-Myc/cyclinD1/Sox2 signaling pathway. When GBM-R cell lines were treated with BMX alone (thin lines) or BMX with TMZ (thick lines), GSK3β (S9) and active β-catenin decreased. The following c-Myc and cyclin D1 also decreased to induce cell cycle arrest and attenuate sternness activity, However, only BMX with TMZ (dashed lines) possibly induce apoptosis. The pathway on the left side: WT-p53 mediated MGMT inhibition. When GBM-R cell lines were treated with BMX alone or BMX with TMZ, WT-p53 increased and downregulated MGMT levels, cell cycle arrest and sternness in both BMX alone (thin lines) and BMX with TMZ (thick lines). However, WT-p53 and DNA damage marker (WT-p53-ser15, not shown) increased the following the activation of cell cycle arrest marker (P21) and proapoptotic markers (BAX/Bcl2, and Puma) to induce apoptosis and cell death only in BMX with TMZ (thick lines), indicating as profoundly DNA damage. Color red indicated up-regulation. Color green indicated down-regulation.

It was found in the example that the BMX provided an enhanced effect in inhibition of HDAC to to decrease MGMT via WT-p53 restoring (all P53 lanes in FIG. 5A-C). It was demonstrated in the present invention that BMX alone (thin lines in the left part) moderately increased WT-p53 level to moderately downregulate MGMT expression, leading to still maintain the ability of DNA repair (FIG. 5B). It was also speculated that HDAC inhibition may reduce MGMT expression through WT-p53 reactivation. It was demonstrated that BMX alone moderately increased the WT-p53 level and moderately downregulated MGMT expression, leading to the maintenance of DNA repair. Moreover, BMX alone also induced cell cycle arrest marker (P21). In the present invention, the combination of BMX and TMZ (thick lines in left part) induced extensive DNA damage through WT-p53 (and ser15) overexpression and downregulated MGMT expression, eventually leading to WT-p53 mediated apoptosis (FIG. 5C). This combination (compared with BMX alone) could also increase the expression of cell cycle arrest marker (P21), proapoptotic proteins (Bax/Bcl2 and Puma) and induce cleaved caspase-3 expression for WT-p53 mediated apoptosis. Taken together, these results implied that BMX (thin lines in left part in FIG. 7) alone only partially induced WT-p53 mediated MGMT inhibition but that the BMX and TMZ combination (thick lines in left part in FIG. 7) enhanced TMZ cytotoxic effect in GBM-R cell lines to overcome TMZ resistance.

In conclusion, it was unexpectedly found in the present invention that BMX overcomes TMZ resistance by enhancing TMZ-mediated cytotoxic effect by downregulating the β-catenin/c-Myc/SOX2 signaling pathway and upregulating WT-p53 mediated MGMT inhibition. These findings indicate that the combination of BMX and TMZ is promising for precision personal treating of TMZ-resistant WT-p53 GBM cells.

Example 2

2.1. Materials and Methods 2.1.1 Cell Lines and Cell Culture

Three CRC cell lines HT29, HCT116 and RKO were used in this study. The American Type Culture Collection (ATCC; Manassas, Va., USA) provided human CRC cell lines HT29 (ATCC HTB-38; mutant TP53, p.R273H; APC frame shift, p. E1554fs; wild type β-catenin), HCT116 (ATCC CCL-247; wild type TP53; wild type APC; deletion β-catenin, p. S45del) and RKO (ATCC CRL-2577; wild type TP53; wild type APC; wild type β-catenin). Three CRC cells lines as listed above were cultured in adherent culture condition, maintained at 37° C. inside the cell incubation containing 5% $CO_2$. The two cell lines of HCT-116 and HT-29 cells were cultured in McCoy's 5A medium with supplemented 10% fetal bovine serum (Gibco; Thermo Fischer Scientific, Grand Island, N.Y., USA)), 1% penicillin and 1% streptomycin. RKO cell was cultured in MEM medium with supplemented 10% FBS, 1% penicillin, 1% streptomycin and 1% sodium pyruvate. The cell cultures were passaged by trypsinization every three days. BM-BMX (BMX), (E)-2-(4-Methoxybenzyloxy)-3-prenyl-4-methoxy-N-hydroxycinamide, was provided by Nature Wise Biotech & Medicals Corporation (Taipei, Taiwan).

2.1.2 Cell Proliferation Assays

We plated 4000 CRC cells per well in 96-well plates and allowed them to adhere overnight. To validate cell line responsiveness to BMX and TMZ monotherapy, the cells were treated with different doses of BMX or TMZ for 24, 48, and 72 hrs. To confirm cell responsiveness to the BMX-TMZ combination, cells were either treated with different doses of TMZ (0-1000 μg/mL) with or without BMX (5 μM) for 24, 48, and 72 hrs or with different doses of BMX (0-10 μM) with or without TMZ (50 μM) for 24, 48, and 72 hrs. Following treatment, the absorption value was measured using a CCK8 kit (Targetmol, Shanghai, China) at the indicated time points. The results are reported as the mean±standard deviation of at least three replicates.

2.1.3 Flow Cytometric Analysis of DNA Cell Cycle

Cells were treated with different doses of BMX (0-10 μM) in the presence or absence of TMZ (50 μM) for 48 hrs. Untreated cells were used as a negative control. All samples were run in triplicate in at least three independent experiments. Flow cytometric analysis for propidium iodide (PI) was performed. For the DNA cell cycle, the cells were trypsinized, centrifuged, washed with phosphate-buffered saline (PBS), and fixed in methanol. The cells were then washed again, and incubated with PI-working solution (10 μg/mL PI and 20 mg/mL RNase A) for 15 min at 37° C. in the dark. Using a flow cytometer (Attune NxT flow cytometer, Thermo Fisher Scientific) the PI fluorescence of 10,000 individual nuclei was calculated. The fractions of the cells in G0/G1, S, G2/M, and sub-G0/G1 phase were analyzed using Attune NxT flow cytometry software and were determined for each histogram as the mean peak fluorescence intensity.

2.1.4 Flow Cytometric Analysis of Apoptosis

Apoptosis induction in different doses of BMX (0-10 μM) in the presence or absence of TMZ (50 μM) was assayed by the detection of membrane externalization of phosphatidylserine with the with the CF®488A Annexin V and PI Apoptosis Kit (Fremont, Calif., USA) following the manufacturer's instructions [16]. All samples were then immediately analyzed by flow cytometry.

2.1.5 Quantitative Real Time RT-PCR

RNA was extracted from the cells ($2 \times 10^5$) using Tissue Total RNA Mini Kit (Geneaid, Taipei, Taiwan) following the manufacturer's instructions. RNA concentration and purity was examined using a NanoDrop® spectrophotometer (Thermo Scientific, Waltham, Mass., USA) at 260-280 nm. Then, cDNA synthesis was performed using the High Capacity cDNA Reverse Transcription Kit (Applied Biosystems), also following the manufacturer's instructions. qPCR reactions were performed in the 7500 Real-time PCR System (Applied Biosystems) using Power SYBR Green PCR Master Mix (Applied Biosystems), according to manufacturer's recommendations, with 18s as the inner reference. The threshold cycle (Ct) values were calculated using the StepOnePlus (Applied Biosystems) software. The relative expression of each mRNA was calculated using the 2-(ΔCt) method. The primer sequences for HDAC8 were as follows:

HDAC8 forward
(SEQ ID NO: 1)
5'-GCGTGATTTCCAGCACATAA-3';

HDAC8 reverse
(SEQ ID NO: 2)
5'-ATACTTGACCGGGGTCATCC-3'.

18s forward
(SEQ ID NO: 3)
5'-TCAAGTGCAGTGCAACAACTC-3';

18s reverse
(SEQ ID NO: 4)
5'-AGAGGACAGGGTGGAGTAATCA-3'.

2.1.6 Colony Formation Assay

For the anchorage-dependent growth assay, 1000 cells were resuspended in the medium and seeded in 6-well plates. The culture media only added in various concentrations of BMX (0-10 μM) in the presence or absence of TMZ (50 μM) were changed every 2-3 days. After 14 days, the media were removed and the cells were washed and fixed with 4% paraformaldehyde for 30 min, and stained with 0.1% crystal violet for 20 min at 25° C. The intensity of crystal violet was quantified by the absorbance of 570 nm after dissolving the stained cells with dimethyl sulfoxide (DMSO). The results are expressed as the average colony±SE from three independent experiments.

2.1.7 Senescence-Associated (SA) β-Galactosidase (SA-β-Gal) Analysis

SA expression of β-gal activity was done with a Senescence Detection kit (CS0030-1KT; Sigma-Aldrich; Merck Millipore, Darmstadt, Germany). Briefly, cells were treated with different doses of BMX (0-10 μM) in the presence or absence of TMZ (50 μM) for 48 hrs, were washed with PBS and fixed using the fixative solution for half an hour at room temperature and then incubated at 37° C. overnight with the SA-β-gal staining solution. SA-β-gal activity was examined by X-gal (5-bromo-4-chloro-3-3indolyl β-D-galactoside) staining at pH 6.0. The senescent cells stained with blue were photographed. Randomly selected fields (n=3) were analyzed by light microscope to quantify the percentage of senescent cells.

2.1.8 Western Blot Analysis

Western blot analysis was used to examine the indicated protein expression levels under various concentrations of BMX (0-10 μM), and SAHA, VPA or PCI-34051 in the presence or absence of TMZ (50 μM) or OXP (5 μM) of the tested cell lines. SDS-PAGE and Western blot analysis was performed on lysates prepared as outlined previously [16]. The specific primary antibodies against acetyl-histone H3 (Lys9/Lys14), acetyl-histone H4 (Lys8), P53, acetyl-p53 (Lys382), phospho-p53 (Ser15), P21, P16, MGMT, phosphor-H2AX (S139), E2F1, E2F3, Cleaved Caspase-3, Cleaved Caspase-8, Cleaved Caspase-7, Cleaved Caspase-9, PARP, Bax, Bcl-2, Bid, Bim, Bak, Puma, β-catenin, phospho-β-catenin(Ser/33/37/41), GSK3β, phospho-GSK3β (Ser 9), c-Myc, Cyclin D1, P62, LC3B, CD133, CD44, SOX-2 and HDAC8 were used for detection, and GAPDH, α-tubulin or β-actin was used as the internal control. After incubation with the primary antibodies, and then incubated with horseradish peroxidase (HRP)-conjugated secondary antibodies, the HRP signals were detected with a chemical HRP substrate. The antibodies we used are listed in Table 4. Signal of each target protein was visualized by incubation with an enhanced chemiluminescent reagent and exposure to X-ray film.

TABLE 4

Key resources

| Reagent Type (Species) or Resource | Designation | Source or Reference | Identifiers | Additional Information |
|---|---|---|---|---|
| Antibody | Rabbit anti-Acetyl-Histone H3(Lys9/Lys14) | Cell signaling (Beverly, MA, USA) | s9677 | 1:1000 |
| Antibody | Rabbit anti-Acetyl-Histone H4(Lys8) | Cell signaling (Beverly, MA, USA) | s2594 | 1:1000 |
| Antibody | Mouse anti-GAPDH | Santa Cruz (Santa Cruz, CA, USA) | sc-32233 | 1:1000 |
| Antibody | Mouse anti-P53 | Santa Cruz (Santa Cruz, CA, USA) | sc-126 | 1:1000 |
| Antibody | Rabbit anti-Acetyl-p53(Lys382) | Cell signaling (Beverly, MA, USA) | s2525 | 1:1000 |
| Antibody | Rabbit anti-Phospho-p53 (Ser15) | Cell signaling (Beverly, MA, USA) | 9284 | 1:1000 |
| Antibody | Rabbit anti-P21 | Cell signaling (Beverly, MA, USA) | s2947 | 1:1000 |
| Antibody | Mouse anti-P16 | Santa Cruz (Santa Cruz, CA, USA) | sc-56330 | 1:1000 |
| Antibody | Rabbit anti-MGMT | Cell signaling (Beverly, MA, USA) | s2739 | 1:1000 |
| Antibody | Rabbit anti-phosphor-H2AX (S139) | Elabscience | E-AB-68087 | 1:1000 |
| Antibody | Mouse anti-E2F1 | Santa Cruz (Santa Cruz, CA, USA) | SC-251 | 1:1000 |
| Antibody | Mouse anti-E2F3 | Santa Cruz (Santa Cruz, CA, USA) | SC-56665 | 1:1000 |
| Antibody | Rabbit anti-Cleaved Caspase-3 | Cell signaling (Beverly, MA, USA) | s9661 | 1:1000 |
| Antibody | Rabbit anti-Cleaved Caspase-9 | Cell signaling (Beverly, MA, USA) | s9501 | 1:1000 |
| Antibody | Rabbit anti-Cleaved Caspase-7 | Cell signaling (Beverly, MA, USA) | s9491 | 1:1000 |
| Antibody | Rabbit anti-Cleaved Caspase-8 | Cell signaling (Beverly, MA, USA) | s9496 | 1:1000 |
| Antibody | Rabbit anti-PARP | Cell signaling (Beverly, MA, USA) | s9542 | 1:1000 |
| Antibody | Rabbit anti-Bax | Cell signaling (Beverly, MA, USA) | s2772 | 1:1000 |
| Antibody | Rabbit anti-Bcl-2 | Cell signaling (Beverly, MA, USA) | s2870 | 1:1000 |
| Antibody | Rabbit anti-Bid | Cell signaling (Beverly, MA, USA) | s2002 | 1:1000 |
| Antibody | Rabbit anti-Bim | Cell signaling (Beverly, MA, USA) | s2819 | 1:1000 |
| Antibody | Rabbit anti-Bak | Cell signaling (Beverly, MA, USA) | s3814 | 1:1000 |
| Antibody | Rabbit anti-Puma | Cell signaling (Beverly, MA, USA) | s4976 | 1:1000 |
| Antibody | Rabbit anti-β-catenin | Cell signaling (Beverly, MA, USA) | s9562 | 1:1000 |
| Antibody | Rabbit anti-Phospho-β-catenin (Ser33/37/41) | Cell signaling (Beverly, MA, USA) | s9561 | 1:1000 |
| Antibody | Rabbit anti-Phospho-GSK3β(Ser 9) | Cell signaling (Beverly, MA, USA) | s9323s | 1:1000 |
| Antibody | Mouse anti-GSK3β | BD Biosciences | 610202 | 1:1000 |
| Antibody | Rabbit anti-c-Myc | Abcam (Cambridge, MA, USA) | ab32072 | 1:1000 |
| Antibody | Mouse anti-Cyclin D1 | Santa Cruz (Santa Cruz, CA, USA) | sc-8396 | 1:1000 |
| Antibody | Mouse anti-α-tubulin | Sigma-Aldrich (St. Louis, MO, USA) | T5168 | 1:5000 |
| Antibody | Mouse anti-P62 | Abcam (Cambridge, MA, USA) | ab56416 | 1:2000 |
| Antibody | Rabbit anti-LC3B | Cell signaling (Beverly, MA, USA) | s3868 | 1:1000 |
| Antibody | Rabbit anti-CD133 | Cell signaling (Beverly, MA, USA) | s64326 | 1:1000 |
| Antibody | Rabbit anti-CD44 | Proteintech (, USA) | 15675-1-AP | 1:2000 |
| Antibody | Rabbit anti-SOX-2 | Abcam (Cambridge, MA, USA) | ab97959 | 1:1000 |
| Antibody | Rabbit anti-HDAC8 | ABclonal | a8865 | 1:1000 |

2.1.9 Statistical Analysis

Data are presented as mean±standard deviation. Statistical analyses were performed using one-way analysis of variance. Data were compared using the student's t test. The level of statistical significance was set at *p<0.05, p<0.01, *p<0.001.

2.2. Result 2.2.1 Optimize the Combination of BMX and TMZ in Three CRC Cell Lines To investigate the influence of BMX or TMZ on CRC cell growth, three human colorectal cancer cell lines, HT29 (p53 mutation), HCT116 (p53 wild type) and RKO (p53 wild type), were utilized. They were separately treated with BMX (0.313, 0.625, 1.25, 2.5, 5 and 10 μM) or TMZ (25, 50, 100, 200, 400, 800 and 1000 μM) for 24, 48 and 72 hrs. The results showed that CRC cell viability was inhibited significantly in a dose-dependent manner. The half maximal inhibitory concentration (IC50) values of BMX or TMZ alone in the HT-29, HCT-116 and RKO cells were derived (Table 5). With clonogenic assay, which represented in vivo tumorigenicity, TMZ was effective against tumor sphere formation in the clonogenic assay of the HT29, HCT116 and RKO cells, the IC50 values of TMZ were 359.45±50.43, 137.66±22.73, and 244.01±29.42 μM, respectively. The results showed that the basic cell proliferation inhibition rate of BMX and TMZ with three incubation time on three colorectal cancer cells including HT-29, HCT-116 and RKO.

chemosensitivity of TMZ. 50 μM TMZ with 5 μM BMX exerted the highest cytotoxic effect in HT-29, HCT-116 and RKO cells. We used this combination in a time dependent manner and noted a cytotoxic effect in 48 hrs. This finding suggested that BMX improved the chemosensitivity of TMZ. BMX in combination with TMZ suppressed cell proliferation in a time-dependent manner. Thus, all subsequent experiments were performed using TMZ 50 μM combined with different concentrations of BMX (2.5, 5 and 10 μM) for 48 hrs.

We next examined colony formation in the presence of BMX alone or combined with TMZ. In regular continuous fashion, we found that this inhibitory effect increased when combined BMX with 50 μM TMZ. If increase to TMZ (150 μM), BMX could be lower down to 1-2 μM instead of 5-10 μM. Taken together, these results have demonstrated the combined use of BMX and TMZ synergistically inhibits proliferation and colony formation of CRC cancer cells. Thus, all subsequent experiments were performed using TMZ 50 μM combined with different concentrations of BMX (2.5, 5 and 10 μM) for 48 hrs.

2.2.2 The Effects of the Combination of BMX and TMZ Compared with Conventional Drugs on CRC Cell cycle arrest is one of the main causes of the inhibition of cell proliferation. To evaluate the possible mechanisms through which BMX or combined treatment inhibited cell growth, cell cycle profiles were assayed using flow cytom-

TABLE 5

BMX and TMZ combination inhibited cell proliferation in CRC cells

| | BMX alone | | | TMZ alone | | |
|---|---|---|---|---|---|---|
| | $IC_{50}$ of BMX (μM) | | | $IC_{50}$ of TMZ (μM) | | |
| | Time(hrs) | | | | | |
| Cell lines | 24 | 48 | 72 | 24 | 48 | 72 |
| HT29 | 42.6 ± 2.4 | 9.9 ± 0.5 | 2.9 ± 0.2 | >1000 | 930.8 ± 47.7 | 257.6 ± 20.53 |
| HCT116 | 24.8 ± 2.5 | 7.7 ± 0.3 | 1.5 ± 0.3 | >1000 | 515.2 ± 21.6 | 192.0 ± 14.7 |
| RKO | 38.5 ± 3.5 | 7.2 ± 0.6 | 1.5 ± 0.2 | >1000 | 991.6 ± 52.4 | 380.5 ± 40.3 |

| | BMX 5 μM was used to combine with different doses of TMZ BMZ (5 μM) | | | TMZ 50 μM combined with different concentrations of BMX TMZ (50 μM) | | |
|---|---|---|---|---|---|---|
| | $IC_{50}$ of TMZ (μM) | | | $IC_{50}$ of BMZ (μM) | | |
| | Time(hrs) | | | | | |
| Cell lines | 24 | 48 | 72 | 24 | 48 | 72 |
| HT29 | >400 | 128.3 ± 18.3 | — | >10 | 9.1 ± 0.2 | 2.2 ± 0.1 |
| HCT116 | >400 | 41.56 ± 2.4 | — | >10 | 3.2 ± 0.3 | 0.9 ± 0.1 |
| RKO | >400 | 21.9 ± 2.7 | — | >10 | 3.6 ± 0.4 | 0.9 ± 0.1 |

To evaluate whether BMX improved the chemosensitivity of TMZ, BMX and TMZ were administered together to HT-29, HCT-116 and RKO cells. The combination of BMX (5 μM) and TMZ (25, 50, 100, 200 and 400 μM) exhibited a greater inhibitory effect on cell growth than BMX and TMZ did individually. The combination of BMX (5 μM) and TMZ (25, 50, 100, 200 and 400 μM) exhibited a greater inhibitory effect on cell growth than BMX and TMZ did individually. Subsequently, TMZ 50 μM combined with different concentrations of BMX (0.313, 0.625, 1.25, 2.5, 5 and 10 μM) were selected to verify that TMZ and BMX suppressed cell proliferation in a time-dependent manner. Notably, BMX decreased the IC50 of TMZ in HT-29, HCT-116 and RKO cells (Table 5). These findings suggested that BMX inhibited CRC cell proliferation and improved the etry. As shown in FIG. 13, the combined treatment significantly induced G2/M phase arrest and exhibited much stronger effects on G2/M phase arrest than any other single drug did in HT29 and HCT116 cells. 2.5, 5 and 10 μM BMX with 50 μM TMZ not only increased the amount of cell cycle arrest in G0/G1 but also caused arrest in the sub G1 phase (apoptosis) in RKO cell lines.

The synergistic effect of BMX with TMZ after a 48 hrs treatment was measured by Annexin V binding in three CRC cells. Treatment with BMX and TMZ induced a prominent increase in apoptotic cell percentage compared with each agent individually. BMX increased early apoptotic cells up to 23.78%, 49.34% and 59.18% in HT29, HCT116 and RKO cells, so did the late apoptosis. While in combination treatment population of late apoptosis increased from 1.08% to 10.36%, 3.67% to 19.37% and 0.32% to 16.48% in HT29, HCT116 and RKO cells after 48 hrs incubation.

2.2.3 BMX, and the Combination of BMX and TMZ Induced Apoptosis were Mediated by p53 Mediated MGMT Inhibition The p53 pathway has been reported to be involved in apoptosis of various cancer cells induced by chemotherapy drugs [28]BMX has been shown to activate p53, leading to cell death, mediated by β-catenin pathway [16]. In order to elucidate the anticancer effect of BMX and TMZ resulted from DNA damage or not, we examined the DNA damage and corresponded p53 pathway markers in three CRC cell lines that had different p53 phenotypes. In view of the basic protein expression status of the markers including p53, Acetyl-p53 (Lyx382), p53(Ser 15), p21, p16, MGMT, γ-H2AX, E2F1, E2F3, GAPDH in HT29, HCT116 and RKO cells, BMX alone not only enhanced p53 expression, but possibly also regulated other important genes interfering with cell growth. Treatment with BMX alone or BMX with TMZ combination dose-dependently increased the levels of p53 phosphorylation (Ser15) and γ-H2AX phosphorylation (Ser139) in HT29, HCT116 and RKO cells. In the HT29, HCT116 and RKO cells, acetylation of p53 at Lys382 increased in a time-dependent manner, enhanced expression of p53 downstream target p21 and p16. As shown in the results of the Western blotting for p53 wildtype and mutant cells, CRC p53 wildtype cells were MGMT hypermethylated and lower the MGMT protein expression as well. In addition, BMX with TMZ combination significantly decreased E2F3 expressions (FIG. 14A). Interestingly, acetylation of histone H3 was also increased by BMX or BMX with TMZ. This suggests that BMX affects the activity of histone acetyltransferases and/or HDACs in cells, which leads to acetylation of proteins, including p53. Combine BMX with TMZ can increase P21, P16 expression and □H2AX phosphorylation through enhancing p53 expression and activating p53 functions mediated MGMT inhibition (FIG. 14A).

The balance between pro-apoptotic (stress or death) signals and anti-apoptotic molecules, including Bcl-2 and Bid, Bax or poma, is a main reason, causing apoptotic response through caspases-dependent pathway [29]. The cleavage of Caspases, exhibited in FIG. 14B, suggested that Caspase-7, Caspase-8, Caspase-9 and Caspase-3 activities showed no significant change in BMX under lower concentrations, while combined with TMZ in HT29 cells, they were highly up-regulated in a dose-dependent manner, contributing to PARP cleavage and apoptosis eventually. Apoptosis protein expression levels of cleaved caspase 3, caspase 7, caspase 9 and caspase PARP were found to significantly increase in a concentration dependent manner following BMX 10 μM treatment in the HCT116 and RKO cell lines. Moreover, we examined the proapoptotic signaling system in p53 wildtype cell mediated apoptosis. The results revealed that the BMX treatment decreased the level of the antiapoptotic proteins Bcl-2 and increase proapoptotic proteins Bax, Bim and Puma. However, BMX treatment did not lead to the upregulation of the proapoptotic Bcl-2 family proteins Bak and Bid. In addition, the synergistic effect of BMX and TMZ was better than BMX along (FIG. 14C). The combination of TMZ plus BMX resulted more senescent cell than each treatment alone, especially in p53 wildtype cell, such as HCT116 and RKO (FIG. 15). Because CD133, CD44, and SOX2 is highly related to the drug resistance of CSCs and is used as a phenotypic marker for CSC including CRC, treatment with BMX and TMZ clearly reduced the expression levels of CD133, CD44 and SOX2 in a dose dependent manner in HT29, HCT116 and RKO (FIG. 16). Thus, the BMX and TMZ combination could enhance the TMZ-mediated cytotoxic effect by attenuating CSC markers to convert the stemness phenotype in CRC cells. Therefore, the results above indicated that caspase-dependent signaling pathway was activated by BMX and TMZ combinational treatment in CRC cells to induce cell apoptosis.

2.4 BMX Enhanced the TMZ Mediated Cytotoxic Effect by Targeting the Wnt/β Catenin/GS10β Pathway in CRC Cells Next, investigated the mechanism by which BMX enhances the TMZ-mediated cytotoxic effect on Wnt/β-catenin activity was investigated in three CRC cells. As shown in FIG. 3A, β-catenin, phospho-β-catenin (Ser33/Ser37/Thr41) and phospho-GSK-3β (Ser9) protein expression levels were increased, while phospho-β-catenin (Ser33/Ser37/Thr41) and phospho-GSK-3β (Ser9) levels were decreased by BMX treatment in three CRC cells. Combined treatment with 5 □M BMX and TMZ reduced the protein levels of β-catenin directly and reduced the protein levels of phospho β-catenin (S33/S37/T41) through phosphorylation by GSK3β in three cell lines. Furthermore, we further examined the effects of BMX on the proliferative markers c-Myc and cyclin D1 and noted that BMX both with and without TMZ could decrease proliferative markers c-Myc and cyclin D1 (FIG. 17A). These results demonstrated that combined treatment with 5 μM BMX and TMZ enhanced GSK3β activity through Ser9 phosphorylation downregulation, which in turn enhanced β-catenin phosphorylation at Ser33/Ser37/Thr41, triggering protein degradation (FIG. 17B). In addition, MG132 application reversed β-catenin degradation and increased MGMT expression under 5 μM BMX and 50 μM TMZ (FIG. 17C). Taken together, these data revealed that BMX and TMZ enhanced TMZ-mediated cytotoxic effects, partly via the Wnt/β-catenin/GSK3β pathway, thus reducing CRC cell proliferation.

Figure 18A:
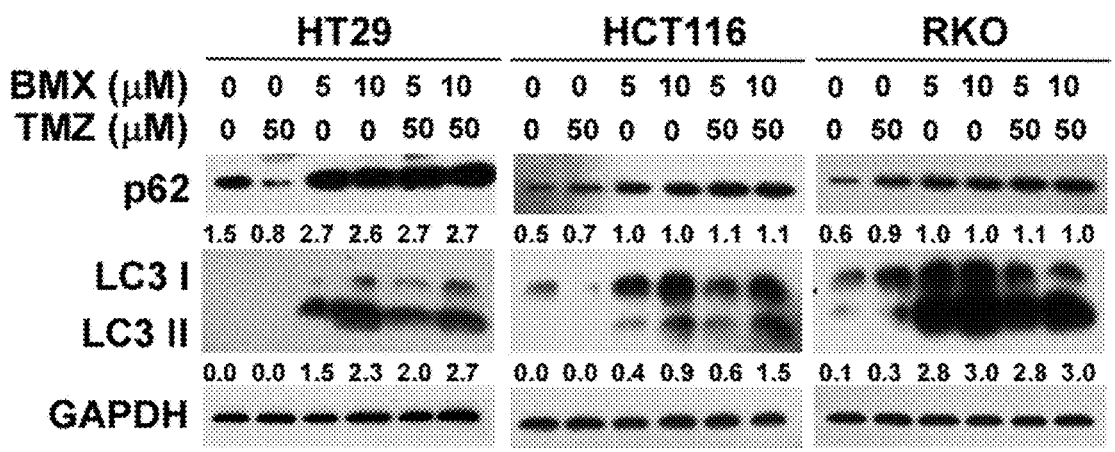
Figure 18B:
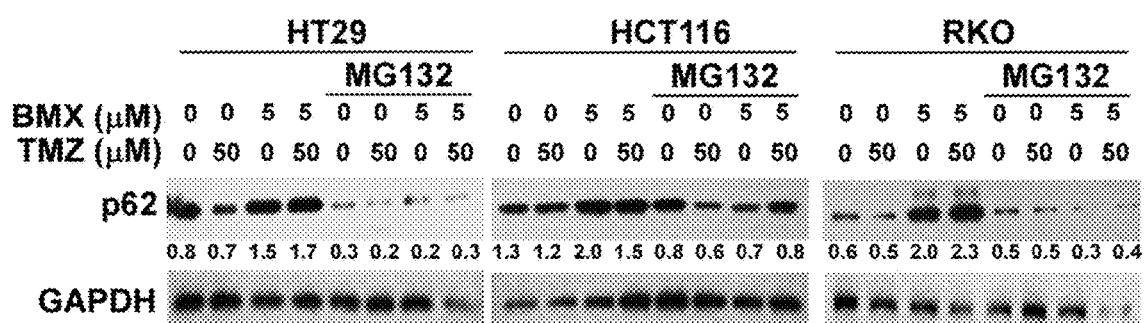
Figure 18C:
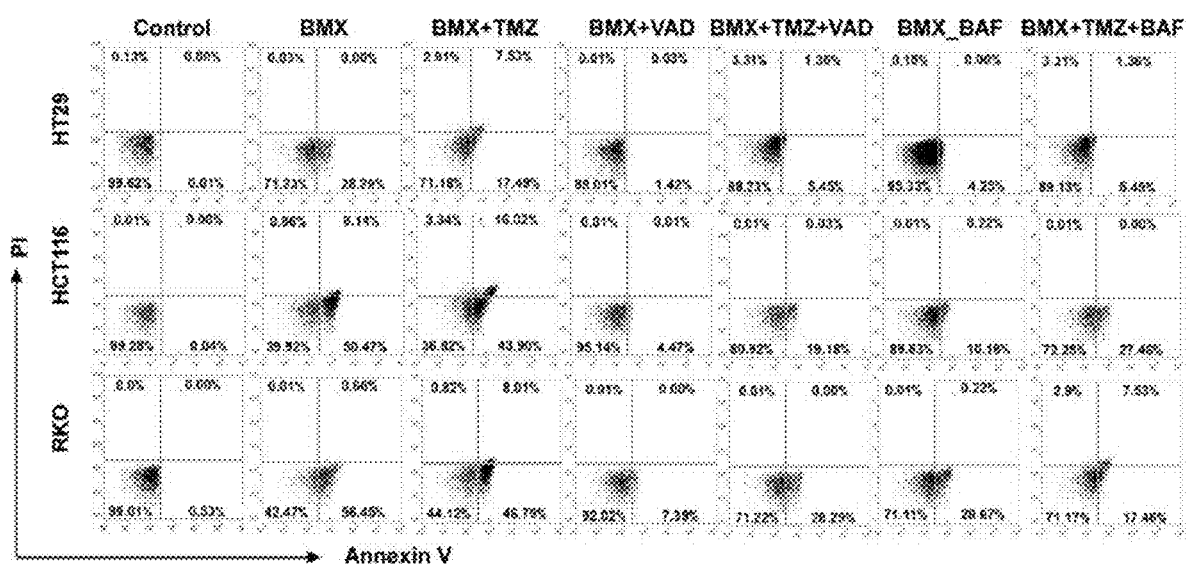
Figure 18D:
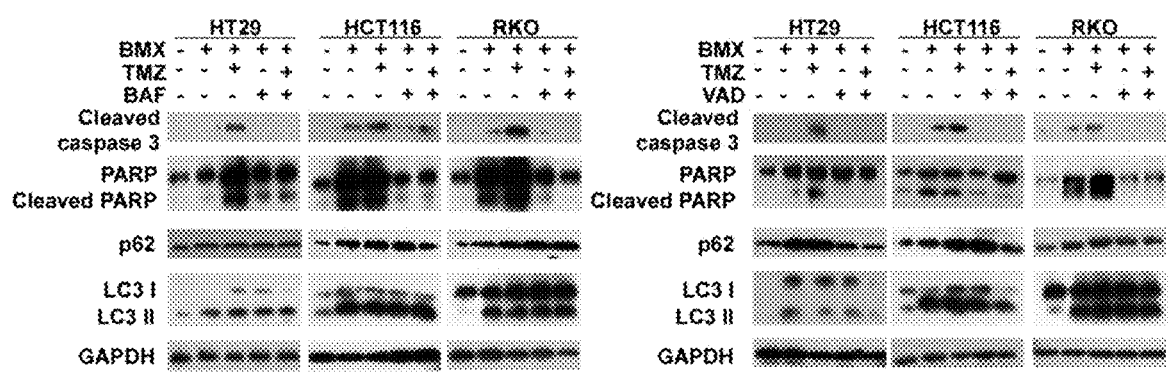

2.5 Autophagy Served as a Key Regulator in BMX, BMX and TMZ Combination Induced Cell Death Lipidated LC3 and autophagy substrate p62 are frequently used as markers to assess autophagosomes and autophagy [17]. Treatment with BMX or combined treatment BMX and TMZ also yielded a concentration-dependent increase in the expression of P62 and LC3-II, which is the processed form of LC3 (FIG. 18A). β-catenin negatively regulates P62 expression [17,30]. To verify that the decreased protein level of P62 was caused by β-catenin protein degradation, the proteasome inhibitor MG132 was applied to the BMX or BMX and TMZ combination treated cells. As expected, BMX induced β catenin degradation was reversed and P62 expression was also suppressed when MG132 was applied (FIG. 18B). Due to β-catenin protein degradation with combination treatment, the P62 was no longer inhibited and then triggered downstream autophagy pathway (FIG. 18B). To determine the role of autophagy in BMX or BMX and TMZ combination-induced cell death, we used BAF, a protein biosynthesis inhibitor that inhibits the late stages of autophagy and Z-VAD-FMK (carbobenzoxy-valyl-alanyl-aspartyl-[O-methyl]-fluoromethylketone), a cell-permeant pan caspase inhibited, to treat cells before BMX or BMX and TMZ combination addition, and we found that Z-VAD-FMK suppressed early apoptosis that induced by BMX plus TMZ treatment in three cell lines. In addition, pre-treatment with BAF Al reduced BMX or BMX and TMZ combination induced cell death obtained via flow cytometry, which was consistent with the results of the reduced expression of cleaved caspase-3, caspase-7, caspase-8 and caspase-9 induced by BMX or BMX and TMZ combination. Interactions between different autophagy/apoptosis related proteins and the corresponding signaling pathways have been identified, implying crosstalk exists between two pathways. To test the role of apoptosis in 6c-induced autophagy, we treated cells with BAF or Z-VAD-FMK before adding BMX or BMX and TMZ combination. As shown in FIG. 18D, although Z-VAD-FMK and BAF showed early apoptosis suppression, BAF inhibited BMX and TMZ combination induced caspase 3 activation without interfering LC3I/II in all cells. However, Z-VAD-FMK inhibited BMX and TMZ combination induced caspase 3 activation with interfering LC3 I/II in p53 mutant type cell line. Taken together, these results emphasized the importance of stimulating autophagy during cell death.

2.3. Conclusion

CRC treatments using traditional radio-chemotherapy are sometimes inefficient, partly because of CRC patients does not respond to this therapy regimen and/or suffer from severe drug toxicities. It is demonstrated in the present invention that the combination of BMX and TMZ exhibited the specific and efficient, synergistic anti-proliferative and apoptotic effect in HCC cells, especially in HCT116 and RKO. In conclusion, BMX and TMZ provided the best synergistic efficacy and its mechanism is the most important link at present. It is also concluded that BMX, a specific HDAC8i, in combination with temozolomide (TMZ) inhibited cell proliferation, induced cell cycle arrest, cell senescence, autophagy and apoptosis, resulting in cell death.

It is also found that the combination of BMX and TMZ induced the synergistic apoptotic cell death through caspase-3 cleavage and PARP activation. It was demonstrated in the present invention that the combination of BMX and TMZ induced augmentation of phospho-p53 (ser15) as well as DNA damage such as increased γ-H2AX foci. The increased expression of phospho-p53 (ser15) might result from the increase in total p53 expression, which was reported in our previous study [16, 17]. In addition, our study revealed that BMX might have an HDAC-dependent synergistic effect with TMZ on the viability of CRC cells.

Given the above, the high HDAC8 expression in human GBM tissues and GBM-R cell lines are correlated with MGMT levels. The combination of BMX and TMZ induced WT-p53 mediated apoptosis through WT-p53 mediated MGMT inhibition in GBM-R cell lines. Moreover, the combination of BMX and TMZ also suppressed cell proliferation and GSC phenotype activity via the β-catenin/c-Myc/cyclin D1/SOX2 signaling pathway in GBM-R cell lines. Therefore, BMX could be a promising strategy for the precision personal treatment of WT-p53 and TMZ-resistant GBM patients.

Overall, as an indication of the synergistic mechanism, it was demonstrated in the present invention that the combination of BMX and TMZ was effective in the induction of cell death of CRC through upregulating p53/p21/E2F3/Bax and downregulating Wnt/β-catenin/cyclin D1/c-Myc/p62 pathways. Therefore, it was found that the combination of BMX and TMX provides the potential effect on cell death, including induction of apoptosis and autophagy. The results in the Examples indicate the potential role of the combination of BMX and TMZ by helping us understand their HDAC8 dependent synergistic effect on CRC cell death. These findings suggest a highly clinically relevant new mechanism of developing resistance against combined chemo-regimens.

While this specification contains many specifics, these should not be construed as limitations on the scope of the invention or of what may be claimed, but rather as descriptions of features specific to particular embodiments or examples of the invention. Certain features that are described in this specification in the context of separate embodiments or examples can also be implemented in combination in a single embodiment.

REFERENCES

1. Louis, D. N.; Perry, A.; Reifenberger, G.; von Deimling, A.; Figarella-Branger, D.; Cavenee, W. K.; Ohgaki, H.; Wiestler, O. D.; Kleihues, P.; Ellison, D. W. The 2016 World Health Organization Classification of Tumors of the Central Nervous System: a summary. Acta Neuropathol 2016, 131, 803-820, doi:10.1007/s00401-016-1545-1.
2. Park, J. K.; Hodges, T.; Arko, L.; Shen, M.; Iacono, D. D.; McNabb, A.; Bailey, N. O.; Kreisl, T. N.; Iwamoto, F. M.; Sul, J., et al. Scale to Predict Survival After Surgery for Recurrent Glioblastoma Multiforme. Journal of Clinical Oncology 2010, 28, 3838-3843, doi:10.1200/jco.2010.30.0582.
3. Stupp, R.; Mason, W. P.; van den Bent, M. J.; Weller, M.; Fisher, B.; Taphoorn, M. J.; Belanger, K.; Brandes, A. A.; Marosi, C.; Bogdahn, U., et al. Radiotherapy plus concomitant and adjuvant temozolomide for glioblastoma. N Engl J Med 2005, 352, 987-996, doi:10.1056/NEJMoa043330.
4. Stupp, R.; Hegi, M. E.; Mason, W. P.; van den Bent, M. J.; Taphoorn, M. J.; Janzer, R. C.; Ludwin, S. K.; Allgeier, A.; Fisher, B.; Belanger, K., et al. Effects of radiotherapy with concomitant and adjuvant temozolomide versus radiotherapy alone on survival in glioblastoma in a randomised phase III study: 5-year analysis of the EORTC-NCIC trial. Lancet Oncol 2009, 10, 459-466, doi:10.1016/s1470-2045(09)70025-7.
5. Siegel, R. L., Miller, K. D., and Jemal, A. (2015) Cancer statistics, 2015. CA Cancer J Clin 65, 5-29
6. Vecchione, L., Gambino, V., Raaijmakers, J., Schlicker, A., Fumagalli, A., Russo, M., Villanueva, A., Beerling, E., Bartolini, A., Mollevi, D. G., El-Murr, N., Chiron, M., Calvet, L., Nicolazzi, C., Combeau, C., Henry, C., Simon, I. M., Tian, S., in't Veld, S., D'Ario, G., Mainardi, S., Beijersbergen, R. L., Lieftink, C., Linn, S., Rumpf-Kienzl, C., Delorenzi, M., Wessels, L., Salazar, R., Di Nicolantonio, F., Bardelli, A., van Rheenen, J., Medema, R. H., Tejpar, S., and Bernards, R. (2016) A Vulnerability of a Subset of Colon Cancers with Potential Clinical Utility. Cell 165, 317-3307. Xie, Y.-H., Chen, Y.-X., and Fang, J.-Y. (2020) Comprehensive review of targeted therapy for colorectal cancer. Signal Transduction and Targeted Therapy 5, 22
8. Floudas, C. S., Brar, G., Mabry-Hrones, D., Duffy, A. G., Wood, B., Levy, E., Krishnasamy, V., Fioravanti, S., Bonilla, C. M., Walker, M., Morelli, M. P., Kleiner, D. E., Steinberg, S. M., Figg, W. D., Greten, T. F., and Xie, C. (2019) A Pilot Study of the PD-1 Targeting Agent AMP-224 Used With Low-Dose Cyclophosphamide and Stereotactic Body Radiation Therapy in Patients With Metastatic Colorectal Cancer. Clin Colorectal Cancer 18, e349-e360.
9. Martino-Echarri, E., Henderson, B. R., and Brocardo, M. G. (2014) Targeting the DNA replication checkpoint by pharmacologic inhibition of Chk1 kinase: a strategy to sensitize APC mutant colon cancer cells to 5-fluorouracil chemotherapy. Oncotarget 5, 9889-9900.
10. Temozolomide [US Prescribing Information]. Whitehouse Station, N.J.; Merck & Co., Inc.; 2019Newlands ES, Stevens MFG, Wedge S R et. al, Temozolomide: a review of its discovery, chemical properties, pre-clinical development and clinical trials. Cancer Treat Rev. 1997; 23(1):35-61.
11. Tatar Z, Thivat E, Planchat E Temozolomide and unusual indications: review of literature. Cancer Treat Rev. 2013; 39(2):125-35.

12. Alonso, M. M.; Gomez-Manzano, C.; Bekele, B. N.; Yung, W. K.; Fueyo, J. Adenovirus-based strategies overcome temozolomide resistance by silencing the O6-methylguanine-DNA methyltransferase promoter. Cancer Res 2007, 67, 11499-11504, doi:10.1158/0008-5472.Can-07-5312.
13. Le Rhun, E.; Preusser, M.; Roth, P.; Reardon, D. A.; van den Bent, M.; Wen, P.; Reifenberger, G.; Weller, M. Molecular targeted therapy of glioblastoma. Cancer Treat Rev 2019, 80, 101896, doi:10.1016/j.ctrv.2019.101896.
14. Cabrini, G.; Fabbri, E.; Lo Nigro, C.; Dechecchi, M. C.; Gambari, R. Regulation of expression of O6-methylguanine-DNA methyltransferase and the treatment of glioblastoma (Review). Int J Oncol 2015, 47, 417-428, doi: 10.3892/ijo.2015.3026.
15. Wiewrodt, D., Nagel, G., Dreimüller, N., Hundsberger, T., Perneczky, A., and Kaina, B. (2008) MGMT in primary and recurrent human glioblastomas after radiation and chemotherapy and comparison with p53 status and clinical outcome. Int J Cancer 122, 1391-1399
16. Tsai, C. Y., Ko, H. J., Chiou, S. J., Lai, Y. L., Hou, C. C., Javaria, T., Huang, Z. Y., Cheng, T. S., Hsu, T. I., Chuang, J. Y., Kwan, A. L., Chuang, T. H., Huang, C. F., Loh, J. K., and Hong, Y. R. (2021) NBM-BMX, an HDAC8 Inhibitor, Overcomes Temozolomide Resistance in Glioblastoma Multiforme by Downregulating the beta-Catenin/c-Myc/SOX2 Pathway and Upregulating p53-Mediated MGMT Inhibition. Int J Mol Sci 22
17. Chu, C. W., Ko, H. J., Chou, C. H., Cheng, T. S., Cheng, H. W., Liang, Y. H., Lai, Y. L., Lin, C. Y., Wang, C., Loh, J. K., Cheng, J. T., Chiou, S. J., Su, C. L., Huang, C. F., and Hong, Y. R. (2019) Thioridazine Enhances P62-Mediated Autophagy and Apoptosis Through Wnt/β-Catenin Signaling Pathway in Glioma Cells. Int J Mol Sci 2019, 20, doi:10.3390/ijms20030473.
18. Bocangel, D.; Sengupta, S.; Mitra, S.; Bhakat, K. K. p53-Mediated down-regulation of the human DNA repair gene 06-methylguanine-DNA methyltransferase (MGMT) via interaction with Sp1 transcription factor. Anticancer Res 2009, 29, 3741-3750.
19. Natsume, A.; Ishii, D.; Wakabayashi, T.; Tsuno, T.; Hatano, H.; Mizuno, M.; Yoshida, J. IFN-beta downregulates the expression of DNA repair gene MGMT and sensitizes resistant glioma cells to temozolomide. Cancer Res 2005, 65, 7573-7579, doi:10.1158/0008-5472.Can-05-0036.
20. Yang, H.-Y., Hsu, Y.-F., Chiu, P.-T., Ho, S.-J., Wang, C.-H., Chi, C.-C., Huang, Y.-H., Lee, C.-F., Li, Y.-S., Ou, G., and Hsu, M.-J. (2013) Anti-cancer activity of an osthole derivative, NBM-T-BMX-OS01: targeting vascular endothelial growth factor receptor signaling and angiogenesis. PloS one 8, e81592-e81592.
21. Chen, T. J., Zhou, Y. F., Ning, J. J., Yang, T., Ren, H., Li, Y., Zhang, S., and Chen, M. W. (2015) NBM-T-BMX-OS01, an Osthole Derivative, Sensitizes Human Lung Cancer A549 Cells to Cisplatin through AMPK-Dependent Inhibition of ERK and Akt Pathway. Cellular Physiology and Biochemistry 36, 893-906.
22. Yang, Y. C.; Chen, C. N.; Wu, C. I.; Huang, W. J.; Kuo, T. Y.; Kuan, M. C.; Tsai, T. H.; Huang, J. S.; Huang, C. Y. NBM-T-L-BMX-OS01, Semisynthesized from Osthole, Is a Novel Inhibitor of Histone Deacetylase and Enhances Learning and Memory in Rats. Evid Based Complement Alternat Med 2013, 2013, 514908, doi:10.1155/2013/514908.
23. Lathia, J. D.; Mack, S. C.; Mulkearns-Hubert, E. E.; Valentim, C. L.; Rich, J. N. Cancer stem cells in glioblastoma. Genes Dev 2015, 29, 1203-1217, doi:10.1101/gad.261982.115.24. Wang, J.; Wang, H.; Li, Z.; Wu, Q.; Lathia, J. D.; McLendon, R. E.; Hjelmeland, A. B.; Rich, J. N. c-Myc is required for maintenance of glioma cancer stem cells. PLoS One 2008, 3, e3769, doi:10.1371/journal.pone.0003769.
25. Gaspar, N.; Marshall, L.; Perryman, L.; Bax, D. A.; Little, S. E.; Viana-Pereira, M.; Sharp, S. Y.; Vassal, G.; Pearson, A. D.; Reis, R. M., et al. MGMT-independent temozolomide resistance in pediatric glioblastoma cells associated with a PI3-kinase-mediated HOX/stem cell gene signature. Cancer Res 2010, 70, 9243-9252, doi: 10.1158/0008-5472.Can-10-1250.
26. Yi, G. Z.; Huang, G.; Guo, M.; Zhang, X.; Wang, H.; Deng, S.; Li, Y.; Xiang, W.; Chen, Z.; Pan, J., et al. Acquired temozolomide resistance in MGMT-deficient glioblastoma cells is associated with regulation of DNA repair by DHC2. Brain 2019, 142, 2352-2366, doi: 10.1093/brain/awz202.
27. Yang, W. B.; Chuang, J. Y.; Ko, C. Y.; Chang, W. C.; Hsu, T. I. Dehydroepiandrosterone Induces Temozolomide Resistance Through Modulating Phosphorylation and Acetylation of Sp1 in Glioblastoma. Mol Neurobiol 2019, 56, 2301-2313, doi:10.1007/s12035-018-1221-7.
28. Jäämaa, S., Af Hällström, T. M., Sankila, A., Rantanen, V., Koistinen, H., Stenman, U. H., Zhang, Z., Yang, Z., De Marzo, A. M., Taari, K., Ruutu, M., Andersson, L. C., and Laiho, M. (2010) DNA damage recognition via activated ATM and p53 pathway in nonproliferating human prostate tissue. Cancer Res 70, 8630-8641.
29. Bogenberger, J. M., Kornblau, S. M., Pierceall, W. E., Lena, R., Chow, D., Shi, C. X., Mantei, J., Ahmann, G., Gonzales, I. M., Choudhary, A., Valdez, R., Camoriano, J., Fauble, V., Tiedemann, R. E., Qiu, Y. H., Coombes, K. R., Cardone, M., Braggio, E., Yin, H., Azorsa, D. O., Mesa, R. A., Stewart, A. K., and Tibes, R. (2014) BCL-2 family proteins as 5-Azacytidine-sensitizing targets and determinants of response in myeloid malignancies. *Leukemia* 28, 1657-1665.
30. Aberle, H., Bauer, A., Stappert, J., Kispert, A., and Kemler, R. (1997) beta-catenin is a target for the ubiquitin-proteasome pathway. *Embo j* 16, 3797-3804.

What is claimed is:

1. A method for treating a TMZ-resistant cancer in a patient, which comprises administering to the patient a therapeutically effective amount of a combination of Temozolomide (TMZ) and a Compound A having the structure of Formula A, or a pharmaceutically acceptable salt or enantiomer thereof:

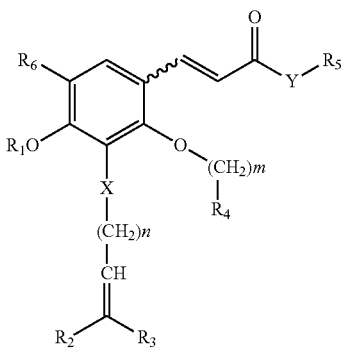

Formula A wherein $R^1$ is hydrogen, alkyl, alkenyl, $C_5$-$C_6$ cycloalkyl, 5-membered or 6-membered unsaturated carbocycle or 5-membered or 6-membered heterocycle, or $(CH_2)_m R^4$;

X is C, —O—, —N— or —S—;

Y is —O—, —NH or —O—$C_1$-$C_4$ alkyl;

n is an integer of 0 to 10;

m is an integer of 0 to 5;

$R^2$ and $R^3$ is independently $C_1$-$C_6$ alkyl;

$R^4$ is $C_5$-$C_6$ cycloalkyl or 5-membered or 6-membered unsaturated carbocycle or heterocycle which may be substituted with halogen, —$CF_3$, —$OR^7$ or —$NR^7R^8$, wherein $R^7$ and $R^8$ are independently hydrogen or $C_1$-$C_6$ alkyl;

$R^5$ is OH, $NH_2$ or $C_5$-$C_8$cycloalkyl, 5-membered or 6-membered unsaturated carbocycle or heterocycle wherein the cycloalkyl, carbocycle and heterocycle may be optionally substituted with halogen, $NH_2$, $NO_2$, $C_1$-$C_6$ alkoxy, $C_{1-6}$ alkylthio, $OR^{7"}$, $NR^7R^8$ or $CF_3$; and $R^6$ is H, $C_1$-$C_{10}$ alkyl which may be substituted by hydroxy or $C_2$-$C_{10}$ alkenyl, or together with $R_1$ being —$C_2H_2$—; and wherein TMZ and the compound A are combined at a relative ratio to effectively overcome TMZ resistance.

2. The method of claim 1, wherein the compound A is a compound BMX having the structure of

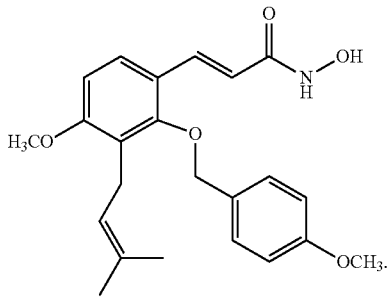

3. The method of claim 1, wherein the compound A provides an efficacy in enhancement of TMZ-mediated cytotoxic effect to overcome the TMZ resistance.

4. The method of claim 3, wherein the enhancement of TMZ-mediated cytotoxic effect is by downregulating the β-catenin/c-Myc/SOX2 signaling pathway and upregulating WT-p53 mediated MGMT inhibition the resistant.

5. The method of claim 1, wherein TMZ and the compound A are separately or sequentially administered.

6. The method of claim 1, wherein the cancer is glioblastoma multiforme (GBM) or colorectal cancer (CRC).

7. A combination for treating a TMZ-resistant cancer in a patient, which comprises TMZ and the compound A as defined in claim 1.

8. The combination of claim 7, wherein the compound A is BMX having the structure of

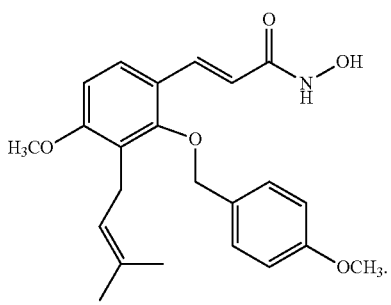

9. The combination of claim 7, wherein the TMZ and compound A are separately or sequentially administered.

10. The combination of claim 8, wherein the TMZ and BMX are separately or sequentially administered.

11. The combination of claim 7, wherein the cancer is glioblastoma multiforme (GBM) or colorectal cancer (CRC).

12. A method for a precision personal treatment for a drug-resistant cancer in a patient, which comprises determining the expression of WT-p53 in the patient, and administering the patient a therapeutically effective amount of the compound A as defined in claim 1 or its combination with said drug if the expression of WT-p53 is present in the patient.

13. The method of claim 12, wherein the drug is TMZ.

14. The method of claim 12, wherein the cancer is glioblastoma multiforme (GBM) or colorectal cancer (CRC).

15. The method of claim 12, wherein the drug-resistant cancer is TMZ-resistant GBM or CRC.

16. The method of claim 12, wherein the compound A is BMX as having the structure of

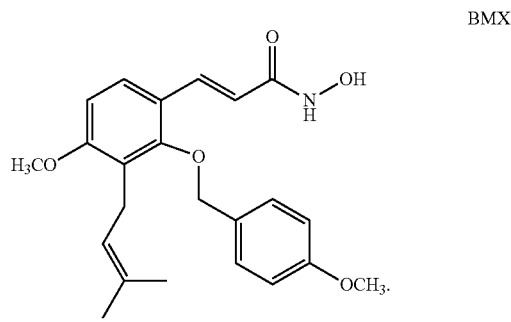 [SMILES: COc1ccc(COc2c(/C=C/C(=O)NO)ccc(OC)c2CC=C(C)C)cc1]

17. The method of claim 12, wherein the compound A provides an efficacy in enhancement of drug-mediated cytotoxic effect to overcome the drug resistance.

18. The method of claim 13, wherein the compound A provides an efficacy in enhancement of TMZ-mediated cytotoxic effect to overcome the TMZ resistance.

19. The method of claim 18, wherein the enhancement of TMZ-mediated cytotoxic effect is by downregulating the β-catenin/c-Myc/SOX2 signaling pathway and upregulating WT-p53 mediated M GMT inhibition the resistant.

* * * * *